United States Patent [19]

Eglitis et al.

[11] Patent Number: 5,672,510
[45] Date of Patent: Sep. 30, 1997

[54] RETROVIRAL VECTORS

[75] Inventors: Martin Eglitis, McLean, Va.; J. Anthony Thompson, Birmingham, Ala.; W. French Anderson, Bethesda, Md.

[73] Assignees: Genetic Therapy, Inc., Gaithersburg, Md.; The United States of America as represented by the Secretary Deptartment of Health and Human Services, Washington, D.C.

[21] Appl. No.: 340,805

[22] Filed: Nov. 17, 1994

Related U.S. Application Data

[63] Continuation of Ser. No. 919,062, Jul. 23, 1992, abandoned, which is a continuation-in-part of Ser. No. 686,167, Apr. 19, 1991, abandoned, which is a continuation-in-part of Ser. No. 467,791, Jan. 19, 1990, abandoned.

[51] Int. Cl.$^6$ .............................. C12N 5/10; C12N 15/79
[52] U.S. Cl. ...................... 435/325; 435/320.1; 435/357
[58] Field of Search ............................ 435/69.1, 172.1, 435/172.3, 320.1, 240.2

[56] References Cited

PUBLICATIONS

Yu, et al., *Proc. Nat. Acad. Sci. USA*, vol. 83, pp. 3194–3198 (May 1986).
Davison, et al., *Methods in Enzymology*, Wu, et al., eds, vol. 153 pp. 34–54 (1987).
Miller, et al., *Bio Techniques*, vol. 7, No. 9, pp. 980–990 (1989).
Palmer, et al., *Blood*, vol. 73, No. 2, pp. 438–445 (Feb. 1989).
Idzerda, et al., *Mol. Cell. Biol.*, pp. 5154–5162 (Nov. 1989).
Quitschke, et al., *J. Biol. Chem.*, vol. 284, No. 16, pp. 9539–9546 (1989).

*Primary Examiner*—David Guzo
*Attorney, Agent, or Firm*—Elliot M. Olstein; Raymond J. Lillie

[57] ABSTRACT

A retroviral vector including a multiple cloning site having no greater than about 70 base pairs, and which includes at least four different enzyme restriction sites, wherein at least two of the sites have an average frequency of appearance in eukaryotic genes of less than one in 10,000 base pairs. Such vector may be employed in conjunction with a shuttle cloning vector having complementary cloning sites to accomplish transfers of genes and/or promoters between the shuttle cloning vector and the retroviral vector. Such a system provides for efficient transfer of genes and/or promoters to a retroviral vector without necessitating reconstruction of the entire retroviral vector. Also contemplated within the scope of the present invention is a retroviral vector having a 3' LTR wherein at least the promoter sequence of the 3' LTR is mutated such that the promoter sequence becomes nonfunctional.

27 Claims, 33 Drawing Sheets

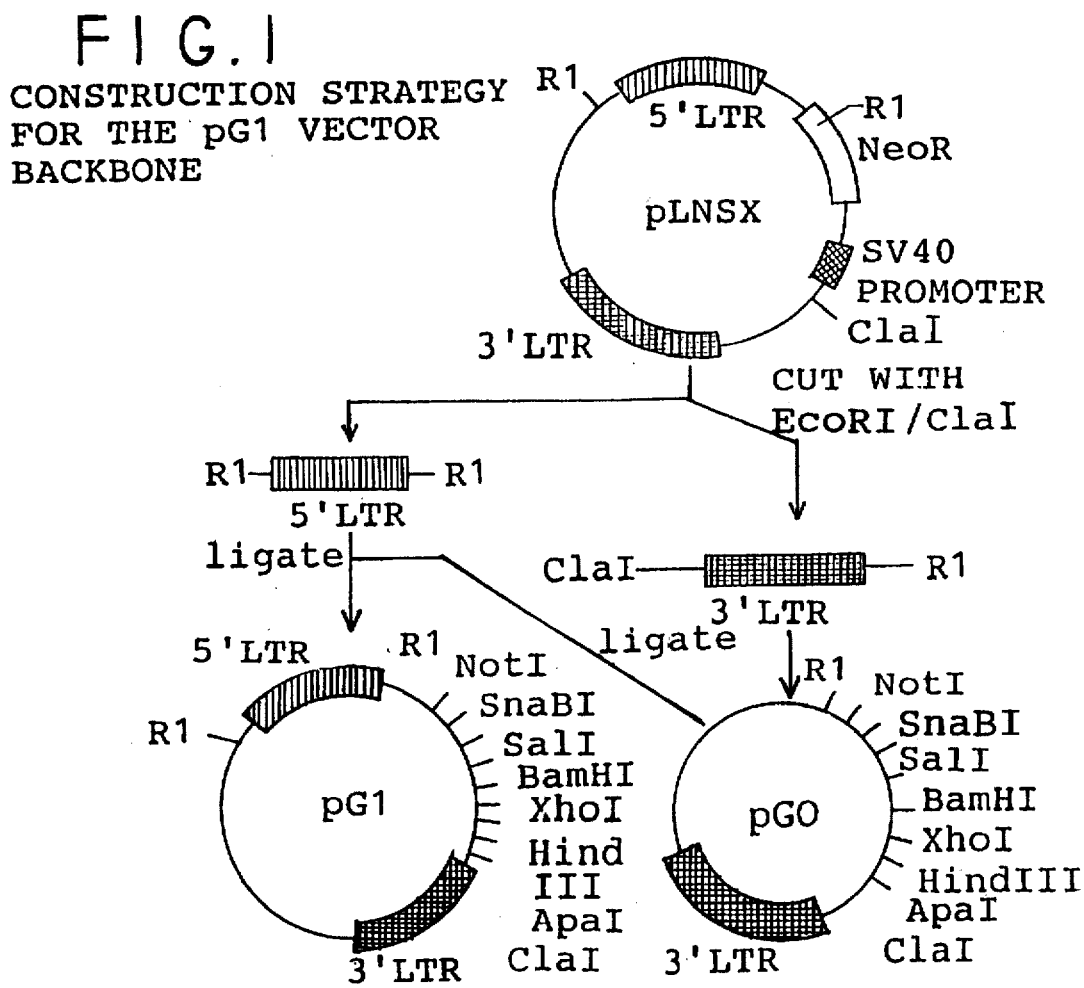
FIG. 1 CONSTRUCTION STRATEGY FOR THE pG1 VECTOR BACKBONE
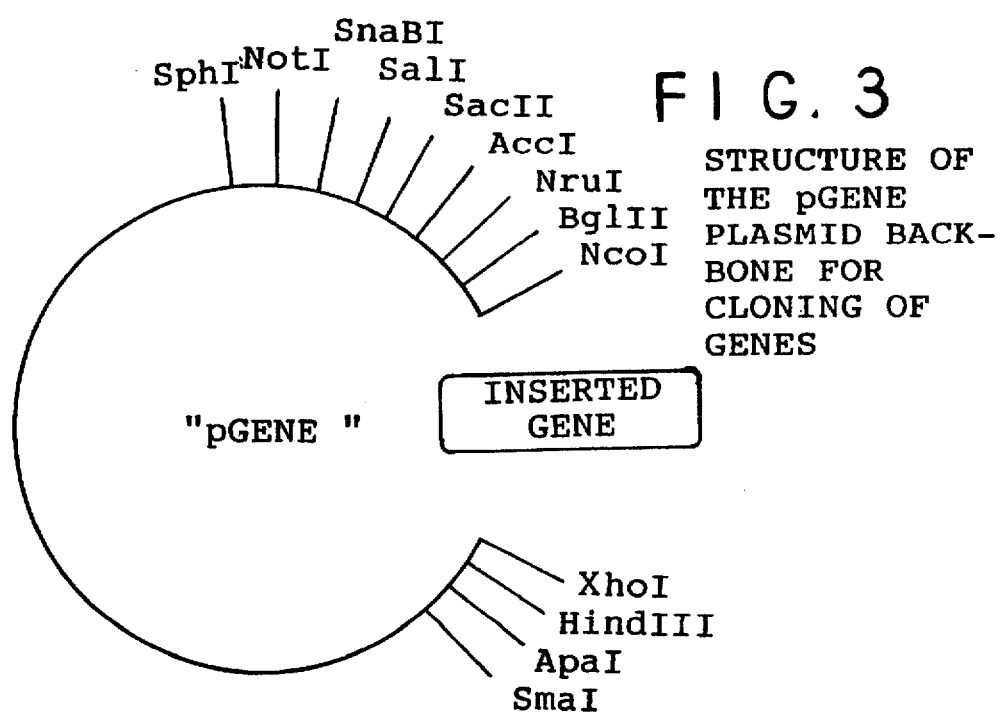
FIG. 3 STRUCTURE OF THE pGENE PLASMID BACKBONE FOR CLONING OF GENES SEQUENCE OF THE MULTIPLE CLONING SITE IN THE pGI PLASMID

| 1/2 EcoRI | NotI | SnaBI | SalI | BamHI | XhoI | HindIII | ApaI |
|---|---|---|---|---|---|---|---|
| AATTC | GCGGCCGC | TACGTA | GTCGAC | GGATCC | CTCGAG | AAGCTT | GGGCCC |
| G | CGCCGGCG | ATGCAT | CAGCTG | CCTAGG | GAGCTC | TTCGAA | CCCGGG |

1/2 ClaI
AT
TAGC

FIG. 2

THE SEQUENCE OF THE MULTIPLE CLONING SITE OF THE pGENE SHUTTLE SYSTEM

| SphI | NotI | SnaBI | SalI | SacII | ACCI | NruI | BglII |
|---|---|---|---|---|---|---|---|
| GGCATG | GCGGCCGC | TACGTA | GTCGAC | CCGCGG | GTCGAC | TCGCGA | AGATCT |
| CCGTAC | CGCCGGCG | ATGCAT | CAGCTG | GGCGCC | CAGCTG | AGCGCT | TCTAGA |

LEADER TRANSLATION       NcoI                          xhoI  HindIII
SEQUENCE INITIATION   CCATGG...INSERTED GENE ...    CTCCAG  AAGCTT
TTCCGCAGCAGCCGGCCA    GGTACC                          GAGCTC  TTCGAA
                      SmaI
AAGGCGTCGTCGGCCGGT ApaI
GGGCCCGGG
CCCGGGCCC

FIG. 4

EXAMPLE OF THE CLONING STRATEGY TO GENERATE A RETROVIRAL VECTOR CARRYING BOTH A MARKER GENE (lacZ, i.e. B-GALACTOSIDASE) AND AN INTERNALLY PROMOTED GENE OF INTEREST (SV40-PROMOTED CD4 Btx)

CONSTRUCTION STRATEGY FOR THE pG2 VECTOR BACKBONE

STRUCTURE OF THE NATURAL MoMuLV LTR AND INDICATED REGION OF ALTERED SEQUENCE

MATCH WITH FIG. 8B

FIG. 8A

```
GCTAGCTTAAGTAACGCCATTTTGCAAGGCATGGAAAAATACATAACTGAGAATA
------+---------+---------+---------+---------+---------+
CGATCGAATTCATTGCGGTAAAACGTTCCGTACCTTTTTATGTATTGACTCTTAT

GTTATTTTAAATTAAAAACACTAACATTCATCTGCATGGAATTGTCTGTATTAAT
------+---------+---------+---------+---------+---------+
CAATAAAATTTAATTTTTGTGATTGTAAGTAGACGTACCTTAACAGACATAATTA

GAAGAATATCTCTTGTCAAAGTTCCATAGGTCTCTTTCTGGTCCCCAGATGCGGTCCAG
------+---------+---------+---------+---------+---------+
CTTCTTATAGAACAGTTCAAGGTATCCAGAGAAAGACCAGGGCTCACGCCAGGTC

CAAGGACCTGAATGACCTGTGCCTTATTTGAACTAAGCCATAAGTTGGCCTCTAG
------+---------+---------+---------+---------+---------+
GTTCCTGGACTTACTGGACACGGAATAAACTTGATTCGGTATTCAACCGGAGATC

ACAACCCCTCACTCGGGGCGCCAGTCCTCCGATTGACTGAGTCGCCCGGG
------+---------+---------+---------+ 450
TGTTGGGGAGTGAGCCCCGCGGTCAGGAGGCTAACTGACTCAGCGGGCCC
```

FIG. 8B

```
         GAGAAGTTCAGAGATCAGGCCCTCAACAACAGTCTTGACAACTTGTAC
         ||||||||||||||||||||||||||||||||||||||||||||||||   100
         CTCTTCAAGTCTCTAGTCCGGGAGTTGTTGTCAGAACTGTTGAACATG

CTAATAAATAAATAGCTTTTTTAAGTTAGTATGTAAATACATTTT
         |||||||||||||||||||||||||||||||||||||||||||||     200
         GATTATTTATTTATCGAAAAAATTCAATCATACATTTATGTAAAA

CCCTCAGCAGTTTCTAGAGAACCATCAGATGTTTCCAGGGTGCCC
         |||||||||||||||||||||||||||||||||||||||||||||     300
         GGGAGTCGTCAAAGATCTCTTGGTAGTCTACAAAGGTCCCACGGG

CGTGTGTTCGGCGCTTCTGCTCCCCCGAGCTCCAGGACAGAGCCC
         |||||||||||||||||||||||||||||||||||||||||||||     400
         GCACACAAGCCGCGAAGACGAGGGGCTCGAGGTCCTGTCTCGGG
```

MATCH WITH FIG. 8A

RETROVIRAL VECTORS

This application is a continuation of application Ser. No. 07/919,062, filed Jul. 23, 1992, now abandoned, which is a continuation-in-part of application Ser. No. 686,167, filed Apr. 16, 1991, now abandoned, which is a continuation-in-part of application Ser. No. 467,791, filed Jan. 19, 1990, now abandoned.

This invention relates to retroviral vectors. More particularly, this invention relates to retroviral vectors having multiple cloning, or restriction enzyme recognition sites, and to systems for the exchange of gene sequences between vectors having compatible or complementary multiple cloning sites.

Retroviral vectors are useful as agents to mediate retroviral-mediated gene transfer into eukaryotic cells. Such vectors are generally constructed such that the majority of sequences coding for the structural genes of the virus are deleted and replaced by the gene(s) of interest.

These new genes have been incorporated into the proviral backbone in several general ways. The most straightforward constructions are ones in which the structural genes of the retrovirus are replaced by a single gene which then is transcribed under the control of the viral regulatory sequences within the long terminal repeat (LTR). Retroviral vectors have also been constructed which can introduce more than one gene into target cells. Usually, in such vectors one gene is under the regulatory control of the viral LTR, while the second gene is expressed either off a spliced message or is under the regulation of its own, internal promoter.

Efforts have been directed at minimizing the viral component of the viral backbone, largely in an effort to reduce the chance for recombination between the vector and the packaging-defective helper virus within packaging cells. A packaging-defective helper virus is necessary to provide the structural genes of a retrovirus, which have been deleted from the vector itself.

Bender et al., *J. Virol.* 61:1639–1649 (1987) have described a series of vectors, based on the N2 vector (Armentano, et al., *J. Virol.*, 61:1647–1650) containing a series of deletions and substitutions to reduce to an absolute minimum the homology between the vector and packaging systems. These changes have also reduced the likelihood that viral proteins would be expressed. In the first of these vectors, LNL-XHC, there was altered, by site-directed mutagenesis, the natural ATG start codon of gag to TAG, thereby eliminating unintended protein synthesis from that point. In Moloney murine leukemia virus (MoMuLV), 5' to the authentic gag start, an open reading frame exists which permits expression of another glycosylated protein (pPr80$^{gag}$). Moloney murine sarcoma virus (MoMuSV) has alterations in this 5' region, including a frameshift and loss of glycosylation sites, which obviate potential expression of the amino terminus of pPr80$^{gag}$. Therefore, the vector LNL6 was made, which incorporated both the altered ATG of LNL-XHC and the 5' portion of MoMuSV. The 5' structure of the LN vector series thus eliminates the possibility of expression of retroviral reading frames, with the subsequent production of viral antigens in genetically transduced target cells. In a final alteration to reduce overlap with packaging-defective helper virus, Miller has eliminated extra env sequences immediately preceding the 3' LTR in the LN vector (Miller et al., *Biotechniques*, 7:980–990, 1989).

The paramount need that must be satisfied by any gene transfer system for its application to gene therapy is safety. Safety is derived from the combination of vector genome structure together with the packaging system that is utilized for production of the infectious vector. Miller, et al. have developed the combination of the pPAM3 plasmid (the packaging-defective helper genome) for expression of retroviral structural proteins together with the LN vector series to make a vector packaging system where the generation of recombinant wild-type retrovirus is reduced to a minimum through the elimination of nearly all sites of recombination between the vector genome and the packaging-defective helper genome (i.e. LN with pPAM3).

Although the LN series of vectors has generated a vector backbone which incorporates several safety features, the LN vector contains a very limited number of potential cloning sites for the insertion of additional genes into the vector.

Gene therapy or drug delivery via gene transfer entails the creation of specialized vectors each vector being applicable only to a particular disease. Thus, it is desirable that a vector cloning system be available which consistently maintains the necessary safety features yet permits maximal flexibility in vector design. Subtle changes in gene position, or in the specific combination of regulatory sequence(s) with the gene of interest, can lead to profound differences in vector titer or in the way that transferred genes function in target cells. Current vector designs require that for each combination of genes and promoters, the entire vector be reconstructed, and even then comparisons between different vectors are difficult because of inconsistencies in the detail of their construction. These inconsistencies in vector structure can also lead to questions of vector safety which need answering on a case by case basis.

It is therefore an object of the present invention to provide a rapid system for the construction of retroviral vectors which also permits consistent vector construction, whereby genes, promoters, or combinations of genes and promoters may be rapidly exchanged and the vectors evaluated to achieve optimal results in tissues of interest.

In accordance with an aspect of the present invention, there is provided a retroviral vector having a multiple restriction enzyme site, sometimes hereinafter referred to as a multiple cloning site, or MCS. The multiple cloning site has a length no greater than about 70 base pairs, and preferably no greater than about 60 base pairs. In general, the multiple cloning site has at least about 20 base pairs, preferably at least about 45 base pairs. Preferably, the multiple cloning site includes at least four cloning, or restriction enzyme sites, wherein at least two of the sites have an average frequency of appearance in eukaryotic genes of less than once in 10,000 base pairs, i.e., the restriction product has an average DNA size of at least 10,000 base pairs.

In general, such restriction sites, also sometimes hereinafter referred to as "rare" sites, which have an average frequency of appearance in eukaryotic genes of less than once in 10,000 base pairs, contain a CG doublet within their recognition sequence, such doublet appearing particularly infrequently in the mammalian genome. Another measure of rarity or scarcity of a restriction enzyme site in mammals is its representation in mammalian viruses, such as SV40. In general, an enzyme whose recognition sequence is absent in SV40 may be a candidate for being a "rare" mammalian DNA cutter.

Examples of restriction enzyme sites having an average frequency of appearance in eukaryotic genes of less than once in 10,000 base pairs include, but are not limited to the NotI, SnaBI, SalI, XhoI, ClaI, SacI, EagI, and SmaI sites. Preferred cloning sites are selected from the group consisting of NotI, SnaBI, SalI, and XhoI.

In general, the multiple restriction enzyme site, or multiple cloning site is located between the 5' LTR and 3' LTR of the retroviral vector. The 5' end of the multiple cloning site is no greater than about 895 base pairs from the 3' end of the 5' LTR, and preferably at least about 375 base pairs from the 3' end of the 5' LTR. The 3' end of the multiple cloning site is no greater than about 40 base pairs from the 5' end of the 3' LTR, and preferably at least 11 base pairs from the 5' end of the 3' LTR.

Such vectors may be engineered from existing retroviral vectors through genetic engineering techniques known in the art such that the resulting retroviral vector includes at least four cloning sites wherein at least two of the cloning sites are selected from the group consisting of the NotI, SnaBI, SalI, and XhoI cloning sites. In a preferred embodiment, the retroviral vector includes each of the NotI, SnaBI, SalI, and XhoI cloning sites.

Examples of retroviral vectors which may be transformed to include the above-mentioned cloning sites include Moloney Murine Leukemia Virus, spleen necrosis virus, and vectors derived from retroviruses such as Rous Sarcoma Virus and Harvey Sarcoma Virus. Specific vectors which may be constructed in accordance with the present invention are described in the examples hereinbelow.

Such a retroviral vector may serve as part of a cloning system for the transfer of genes to such retroviral vector. Thus, in accordance with another aspect of the present invention, there is provided a cloning system for the manipulation of genes in a retroviral vector which includes a retroviral vector including a multiple cloning site of the type hereinabove described, and a shuttle cloning vector which includes at least two cloning sites which are compatible with at least two cloning sites selected from the group consisting of NotI, SnaBI, SalI, and XhoI located on the retroviral vector. The shuttle cloning vector also includes at least one desired gene which is capable of being transferred from said shuttle cloning vector to said retroviral vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector can be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBr322; pUC 18; etc.

Although the scope of the present invention is not to be limited to any theoretical reasoning, the present invention provides for retroviral vectors having a larger choice of cloning sites, and shuttle vectors with complementary cloning sites, which provides for the rapid exchange of genes and/or promoters from the shuttle vector to the retroviral vector. The increased number of cloning sites also provides for greater flexibility in vector construction.

In addition, the NotI, SnaBI, SalI, and XhoI cloning sites are sites which are of extreme rarity in eukaryotic genes. The use of such "rare" sites enables one to extract a first gene from the retroviral vector, and replace the first gene with a second gene without altering the retroviral vector backbone structure. Thus, reconstruction of the entire retroviral vector is not necessary. To aid in the effective transfer of genes and/or promoters between the retroviral vector and the shuttle vector, it is preferred that the order of the cloning sites in the retroviral and shuttle vectors be complementary. Through such exchange of genes and promoters, vectors are constructed which may be efficiently evaluated to achieve optimal results in tissues of interest.

In accordance with another aspect of the present invention, there is provided a retroviral vector, said vector including a 5' LTR (long terminal repeat) and a 3' LTR. At least the promoter sequence(s) of the 3' LTR is mutated, or altered, such that the promoter sequence becomes nonfunctional. Such a mutation, however, does not alter the overall structure of the LTR. In a preferred embodiment, the enhancer sequence(s) of the 3' LTR may also be mutated such that the enhancer sequence(s) also becomes nonfunctional. The integrator sequence, however, is maintained. Thus, when such a vector is introduced into a target cell, viral replication duplicates portions of the 3' LTR to both the 5' and 3' ends of a proviral integrant. The mutation, therefore, causes a "flipping" of the vector whereby the 5' LTR now lacks regulatory sequences, and introduced genes are completely under the regulation of their own promoters. It is also preferred that, in mutations of the 3' LTR as hereinabove described, that the approximate number of base pairs of the original 3' LTR is maintained in the mutated 3' LTR, and approximately the same proportions of types of base pairs of the original 3' LTR is maintained in the mutated 3' LTR.

Although the scope of this aspect of the present invention is not to be limited to any theoretical reasoning, the altering or mutating of only the promoter or enhancer sequences of the 3' LTR does not require a large deletion of the 3' LTR to eliminate promoter or enhancer function, and the overall structure of the 3' LTR is preserved. Because LTR structure is critical for efficient integration of the vector into the genome, one is able to maintain a high titer of retroviral vector. Such vectors, therefore, may be useful in clinical applications where the maintenance of a high titer of vector is essential or critical. Such a retroviral vector may be formed from a retroviral vector, having a multiple cloning site of a length no greater than about 70 base pairs, as hereinabove described, and having at least four cloning sites, wherein at least two of the cloning sites are selected from the group consisting of NotI, SnaBI, SalI, and XhoI; however, the scope of the present invention is not to be limited to such vectors, nor is the scope of this aspect of the present invention limited to vectors having multiple cloning sites. Examples of vectors whose promoter sequence of the 3' LTR may be mutated include Moloney Murine Leukemia Virus, spleen necrosis virus, and vectors derived from retroviruses such as Rous Sarcoma Virus and Harvey Sarcoma Virus. Such mutations, whereby the promoter or enhancer sequences of 3' LTR are altered, may be effected through techniques known in the art.

The invention will now be further described with respect to the following Examples; however, the scope of the present invention is not intended to be limited thereby.

BRIEF DESCRIPTION OF THE DRAWINGS

FIG. 1. Construction strategy for the pC1 vector backbone.

FIG. 2. Sequence of the multiple cloning site in the pC1 plasmid.

FIG. 3. Structure of the pGENE plasmid backbone for cloning of genes.

FIG. 4. The sequence of the multiple cloning site of the pGENE shuttle system.

FIG. 8. Nucleotide sequence of the altered MoMuLV LTR.

EXAMPLE 1

Figure 5:
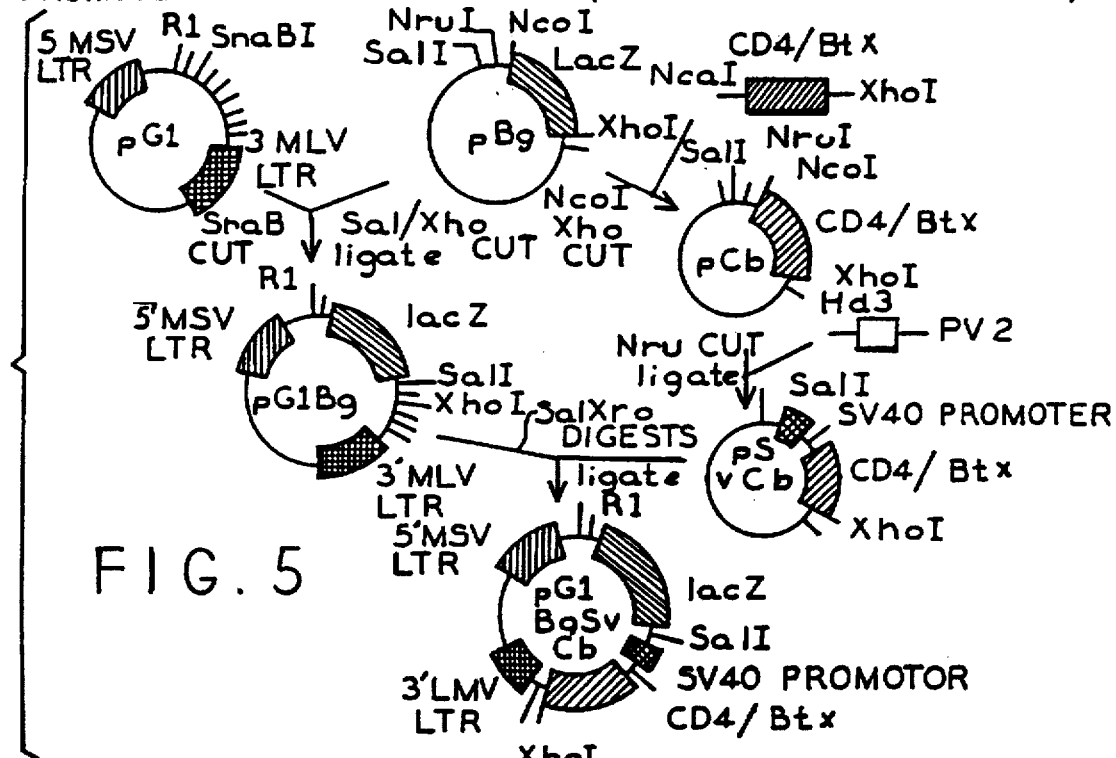
FIG. 5. Example of the cloning strategy used to generate a retroviral vector carrying both a marker gene (LacZ, i.e. beta-galactose) and an internally promoted gene of interest (SV40-promoted CD4-Btx).

Plasmid pG1 was constructed from pLNSX (Palmer et al., Blood, 73:438–445; 1989). The construction strategy for plasmid DG1 is shown in FIG. 1. The 1.6 kb EcoRI fragment, containing the 5' Moloney Sarcoma Virus (MoMuSV) LTR, and the 3.0 kb EcoRI/ClaI fragment, containing the 3' LTR, the bacterial origin of replication and the ampicillin resistance gene, were isolated separately. A linker containing seven unique cloning sites was then used to close the EcoRI/ClaI fragment on itself, thus generating the plasmid pGO. The plasmid pGO was used to generate the vector plasmid pG1 by the insertion of the 1.6 kb EcoRI fragment containing the 5' LTR into the unique EcoRI site of pGO. Thus, pG1 consists of a retroviral vector backbone composed of a 5' portion derived from MoMuSV, a short portion of gag in which the authentic ATG start codon has been mutated to TAG (Bender et al. 1987), a 54 base pair multiple cloning site (MCS) containing from 5' to 3' the sites EcoRI, NotI, SnaBI, SalI, BamHI, XhoI, HindIII, ApaI, and ClaI, and a 3' portion of MoMuLV from base pairs 7764 to 7813 numbered as described in (Van Beveren et al., Cold Spring Harbor, Vol. 2, pg. 567, 1985). (FIG. 2). The MCS was designed to generate a maximum number of unique insertion sites, based on a screen of non-cutting restriction enzymes of the pG1 plasmid, the neo$^R$ gene, the β-galactosidase gene, the hygromycin$^R$ gene, and the SV40 promoter.

The pGene plasmid (FIG. 3) does not exist as an independent molecular entity, but rather may be considered a construction intermediate in the process of cloning genes for subsequent insertion into pG1. The basic backbone is that of pBR322 (Bolivar et al., Gene, 2:95 1977). To the 2.1 kb EcoRI/NdeI fragment containing the ampicillin resistance gene and the bacterial origin of replication two linkers were ligated. These linkers, synthesized using an oligo-nucleotide synthesizer, contain a total of 14 unique restriction enzyme recognition sites, as well as sequences felt to enhance mRNA stability and translatability in eukaryotic cells. The restriction sites were chosen based on a screen of non-cutting restriction enzymes of the plasmid backbone, the neo$^R$ gene, the β-galactosidase gene, the hygromycin$^R$ gene, and the SV40 promoter. Genes can be ligated into this backbone with NcoI and XhoI ends. The resulting backbone, less the inserted gene, is roughly 2.1 kb in size and contains a 99 base pair multiple cloning site containing, from 5' to 3', the following restriction enzyme recognition sites: SphI, NotI, SnaBI, SalI, SacII, AccI, NruI, BglII, NcoI, XhoI, HindIII, ApaI, and SmaI (FIG. 4). From the BglII to the NcoI sites lies a 27 base pair region containing an mRNA signal based on the work of Hagenbuchle et al. Cell, 13:551–563 (1978). It has been found that the 3' terminal sequence of 18S ribosomal RNA is highly conserved among eukaryotes, suggesting that complementary sequences between 18S RNA and mRNA may be involved in positioning the initiating start codon (AUG) on the 30S ribosome. Synthesis of adenovirus 2 late proteins, particularly polypeptide IX, may also follow this rule (Lawrence and Jackson, J. Molec. Biology, 162:317–334 1982). Following this ribosomal binding signal, a consensus signal for initiation of translation based on Kozak's rules (Kozak, Nucl. Acids Res., 12:857–872 (1984)) was also inserted. The wobble at the ATG was used which permitted use of an NcoI restriction enzyme site.

In general, genes may be inserted in between the NcoI and XhoI sites. Promoters may then be added by insertion into the NruI site, if the restriction enzyme map of the inserted gene leaves this site as unique. However, the construction of the multiple cloning site is such that even if some sites no longer remain unique after a gene is inserted, there is a substantial likelihood that sites 5' of the BglII site remain available for promoter insertions. Once a promoter/gene assembly is completed, the entire combination may be removed for insertion into the pG1 backbone. Generally, this has been accomplished by using the complementary SalI and XhoI sites of both the pGene backbone and pG1; however, enough sites are included in the multiple cloning site to generally ensure that, by simple directional cloning, promoter/gene combinations may easily be inserted into the pG1 backbone.

As an example of the utility of the pGene/pG1 system, the generation of several vectors is described. The first is called pG1N2SvBg, a vector using the bacterial neomycin resistance (neo$^R$) gene as a selectable marker and also containing the bacterial β-galactosidase (β-gal) gene under regulation of the SV40 early promoter. First, a 769 base pair EagI/HincII fragment containing all but the very 5' portion of the neo$^R$ gene was isolated from the plasmid pMC1Neo (Thomas end Capecchi, Cell 51:503–512 (1987)). To this fragment was ligated a 50 base pair SphI/EagI linker. This linker restored all of the 5'-most codons of the neo$^R$ gene, and created an NcoI site at the authentic ATG start codon. This fragment was then blunted using the Klenow polymerase, end ligated into pG1 at the unique SnaBI site, generating pG1N2. The second step in the generation of the pG1N2SvBg vector was the construction of pBg, that is the pGene backbone with the β-gal gene inserted into the multiple cloning site. The 3.0 kb BamHI/EcoRI fragment of the lacZ gene encoding β-galactosidase was isolated and two linkers were added. To the 5' end an NdeI-BamHI linker, containing the 5' portion of the multiple cloning site up to the NcoI site, as well as the first 21 base pairs of the lacZ gene, was ligated. To the 3' end, an EcoRI/EcoRI linker completing the 3' sequence of the lacZ followed by sequence encoding the XhoI, HindIII, ApaI, and SmaI sites was ligated. The sequence of the 5' EcoRI site was mutated, maintaining amino acid coding fidelity but eliminating the internal EcoRI site to permit directional cloning and screening of the total linkered lacZ fragment into the 2.1 kb NdeI/EcoRI of pBR322. The pBg plasmid was then used to construct an SV40 promoted β-gal gene. The 339 base pair PvuII/HindIII SV40 early promoter fragment was then inserted into both pBg in the unique NruI site to generate the plasmid pSvBg. Once pSvBg was obtained, it was a simple matter to obtain the SalI/XhoI fragment containing the SV 40- promoted lacZ gene and insert it into SalI/XhoI digested pG1N2, thereby generating pG1N2SvBg.

Vector producer cell lines were prepared using established protocols. The packaging cell line PE501 (Miller and Rosman, *Biotechniques* 7:980–990 (1989)) was plated at a density of 5×10⁵ cells per 100 mm plate and the following day purified vector DNA was introduced using standard CaPO₄ precipitation (Wigler et al., *Cell* 14725–731 (1978)). For each plate of cells to be transfected, 20–40 µg of vector DNA was prepared with a co-precipitate consisting of 0.25M CaCl₂/1 mM Hepes (pH 7.2) and 140 mM NaCl, 0.75 mM Na₂HPO₄, 25 mM Hepes (pH7.2). The DNA/precipitate was allowed to sit at room temperature for 30 min and then added (1 ml/plate) to the cells in tissue culture medium (DMEM+10% fetal Bovine serum) for an overnight incubation. The medium was changed to fresh DMEM+ serum the following morning. The transfected cells were allowed to grow to near confluence for the next 48 hours, at which point virus supernatant was collected to infect a separate population of PA317 vector packaging cell lines (ATCC No. CKL9078) at a density of 1×10⁵ cells per 100 mm plate seeded 24 hours prior to infection. The standard infection conditions include undiluted virus supernatant, filtered through a 0.2 uM membrane, to which 8 ug/ml polybrene is added. The transduced cells can then be analyzed directly based on β-gal expression or be selected with the neomycin analogue, G418 sulfate, to enrich for cells expressing the neoʳ gene.

When G418 resistant trans-infected clones appeared, these were collected and grown up by expansion through a series of tissue culture vessels until a population great enough (over 1×10⁶ cells) was generated that titer could be determined. Between 10 and 20 clones were evaluated for the number of G418-resistance conferring particles they generated (i.e. "titered"). Titers based on G418 resistance were performed using standard titering methods (Eglitis et al., *Science* 230:1395–1398 (1985)). Briefly, NIH 3T3 cells were plated at a density of 2×10⁴ cells per 35 mm dish and the following day infected for 2–4 hours with various dilutions of virus supernatant containing 8 ug/ml polybrene. The cells were allowed to grow for an additional 24–48 hours following infection and then were grown in selective medium containing G418 (800 ug/ml) for 10–12 days prior to staining with methylene blue and counting individual G418 resistance colonies. Producer clones were identified which generated between 5×10⁴ and 5×10⁵ G418 resistant colony-forming units per ml.

The ability of the G1N2SvBg vector to transduce cells with a functional bacterial lacZ gene was established by detecting β-gal activity after reaction with the chromogenic substrate 4-Cl-5-Br-3indolyl-β-galactoside (X-gal). The X-gal staining procedure has been described in detail previously by Sanes et al. *EMBO* 5:3133–3142 (1986). The NIH 3T3 target cells are plated and infected with viral supernatant as described above. Infected cells are passed at a dilution of 1:20 48 hours post-infection and allowed to grow to confluence. When confluent, plates are rinsed with PBS, briefly fixed with 2% formaldehyde plus 0.2% glutaraldehyde in PBS and incubated overnight at 37° C. with a reaction mixture containing 1 mg/ml X-gal. Distinct patches or "colonies" of blue cells, which arise clonally from individual infected cells, will then be visible if the vector confers the expression of active β-gal enzyme.

In other examples of the utility of the pGene/pG1 system, the strategy for the generation of two vectors is described. The first is called pG1BgSvCb, a vector using the bacterial β-galactosidase gene as a selectable marker and also containing a marked truncated CD4 gene under regulation of the SV40 early promoter. The second is called pG1BgSvCd, a vector similar to pG1BgSvCb but encoding instead the native soluble CD4. The first step in the generation of these vectors is the insertion of the 3.0 kb NcoI/XhoI fragment containing the lacZ gene obtained from pBg (see above) and inserting it by blunt ligation into the SnaBI site of pG1, thereby generating pG1Bg.

The pBg plasmid is also used to construct an SV40 promoted, truncated CD4 gene. The construction is begun with the 534 base pair HaeII/NheI fragment of the CD4 gene encoding the amino terminal 178 amino acids of the CD4 receptor. To the 5' end of this fragment is ligated an NcoI/HaeII linker encoding the 23 amino acid leader sequence of CD4, including the authentic ATG start codon. To the 3' end is ligated, in one case, a 45 base pair NheI/XhoI linker encoding for the bungarotoxin binding domain of the acetylcholine receptor (Btx). This binding domain provides a very sensitive radio-assay for the presence of the secreted CD4 protein. The resulting 601 base pair NcoI/XhoI CD4/Btx fragment is inserted into pBg into the place of the NcoI/XhoI fragment of the lacZ gene to result in the plasmid pCb. In a second case, to the 3' end was ligated a 30 base pair NheI/HindIII linker coding for six natural CD4 amino acids, followed by a repetitive stop signal. This 586 base pair NcoI/HindIII natural CD4 fragment was also inserted into pBg into the place of the NcoI/HindIII fragment of the lacZ gene to result in the plasmid pCd. The 339 base pair PvuII/HindIII SV40 early promoter fragment was then inserted into both pCb and pCd in the unique NruI site to generate the plasmids pSvCb and pSvCd. To generate the final pG1BgSvCb and pG1BgSvCd vectors, the SalI/XhoI fragment of pSvCb containing the SV40 promoted CD4/Btx gene or the similar SalI/HindIII fragment of pSvCd were individually ligated to the large SalI/XhoI fragment of pG1Bg. The cloning strategy for generating retroviral vector pG1BgSvCb is shown in FIG. 5.

The cloning strategy for three other vectors, pG1N2SvI2, pG1N2SvIl1, and pG1N2SvIll provide further examples of the utility of the pGene/pG1 system. All of these vectors may be easily derived directly from pG1N2SvBg, described above, with the gene for β-gal replaced by one for interleukin-2 (IL-2), interleukin-1 (IL-1), or tumor necrosis factor-α (TNF), respectively. The IL-2 gene is derived from the plasmid HT-5.1 (ATCC #59396). The 1.0 kb BamHI fragment is isolated from this plasmid and then truncated down to a 445 base pair HgiAI/DraI fragment. To restore the authentic 5' coding sequence, a 100 base pair linker is constructed including the entire 20 amino acid coding region of the amino-terminal end of IL-2, and then a 40 base pair stretch identical in sequence to that of pGene between the BglII and NcoI sites is added as a 5' leader. A SnaBI site is added 5' to the BglII, permitting direct insertion of this reconstructed IL-2 fragment into pBg which has been digested with SnaBI and HindIII (the HindIII blunted with the Klenow polymerase). From this resulting pI2 plasmid, a 550 base pair BglII/ClaI fragment is isolated and then inserted into BglII/ClaI digested pG1N2SvBg in the place of the lacZ gene.

The vector pG1N2SvIll is constructed using a commercially available IL-1 gene obtained from Beckman (catalogue number 267408). The gene is isolated as a 499 base pair NcoI/EcoRI fragment and inserted in the place of the lacZ gene in NcoI/EcoRI digested pBG. An 87 base pair oligomer containing the rat growth hormone secretion signal is then inserted into the NcoI site. The resulting gene can then be removed as a 586 base pair BglII/BamHI fragment, filled in with Klenow polymerase, and inserted into pG1N2SvBg. The lacZ gene of pG1N2SvBG is removed by digestion with BglII and XhoI, followed by filling in with Klenow polymerase. These few, simple steps thus yield the final pG1N2SvIll final vector.

As a final example, pG1N2SvTll is constructed similarly. Starting with a commercially available plasmid (Beckman catalogue number 267430), the TNF gene is isolated as a 521 NcoI/EcoRI fragment, inserted in the place of the lacZ gene in NcoI/EcoRI digested pBG and has added the identical rat growth hormone secretion signal described above. The resulting gene is then removed as a 608 base pair BglII/BamHI fragment, and inserted into pG1N2SvBg digested with BglII and XhoI as described above. This emphasizes how, by using pBG as an intermediate, several different genes can rapidly and identically be inserted into the same vector backbone, in this case to generate pG1N2SvTll.

Thus, by a simple process involving minimal steps, fragments of plasmids may rapidly be exchanged and new vectors can be constructed. If regulation by a different promoter is desirable, a variety of strategies would be available. In the instance of pSvCb, the SV40 promoter could be removed and replaced by an alternative. Also, an entire series of promoters could be inserted into the identical NruI site of pCb, or the NcoI/XhoI fragment containing the CD4/Btx gene could be removed from pCb and put in the place of a gene running off a different promoter (eg., β-galactosidase regulated by the Cytomegalovirus promoter, exchanging CD4/Btx for β-galactosidase). This last method requires, for maximal efficiency, that the gene with the different promoter is in the pGene backbone.

EXAMPLE 2

Figure 6:
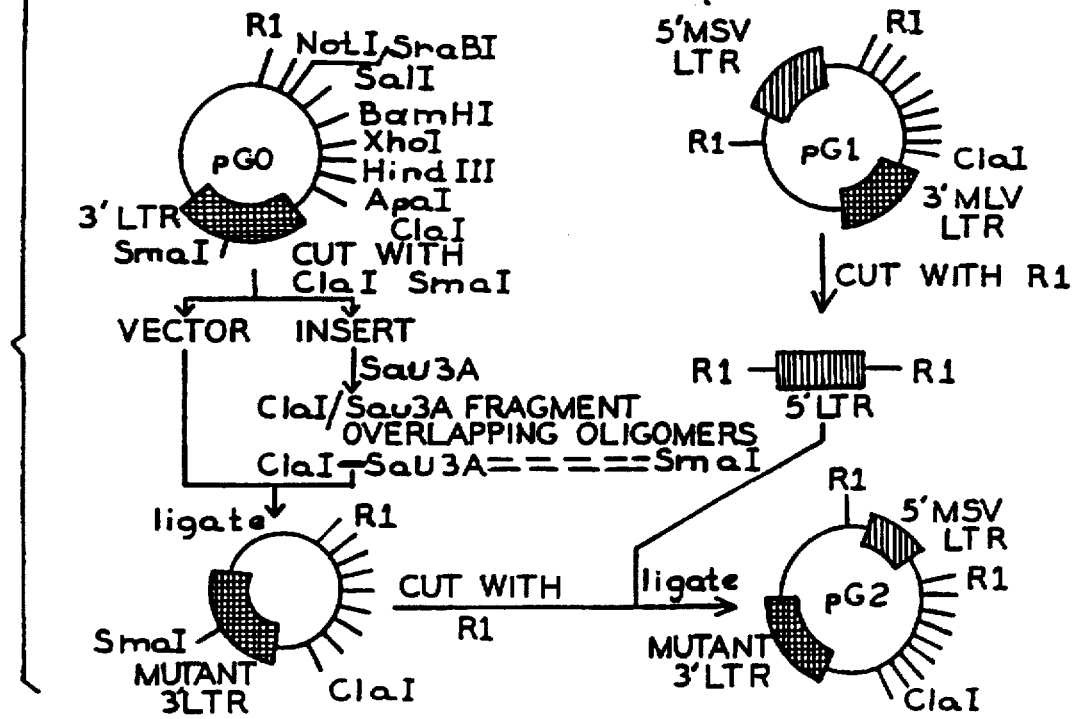
FIG. 6. Construction strategy for the pG2 vector backbone.

To create an example of a retroviral vector system which provides for more accurate regulation of internal genes a derivative of pG1 called pG2 was constructed. A construction strategy for pG2 is shown in FIG. 6. The difference between pG1 and pG2 is a series of sequence alterations in the 3' LTR which eliminate all enhancer and promoter function without altering the overall structure of the LTR. When a vector is introduced into a target cell, viral replication duplicates the U3 and R portions of the 3' LTR to both the 5' and 3' ends of the proviral integrant. The U3 portion of the LTR is 449 base pairs in length and incorporates several regions of strong enhancer activity. Also in the U3 region are sequences capable of binding several transcriptional regulatory proteins, as well as sequences of the consensus distal and proximal promoter signal regions (i.e., the CAAT and TATA boxes). The R portion of the LTR is 70 base pairs in length and contains the signal for polyadenylation of transcribed mRNAs. In addition, the R portion is a region of strong ribosomal binding and is the region where transcription regulated by the promoter in the U3 portion is initiated. As such, the 5' end of R represents the "cap site" for the transcribed viral RNAs. Since the 5' LTR is now lacking its own regulatory sequences, introduced genes are completely under the regulation of their own promoters. This enables the construction of vectors with gene expression optimized for particular target cell types. This differs from previous attempts to disable retroviral regulatory sequences in that other efforts relied on large deletions of the LTR to eliminate the retroviral enhancer and/or promoter. Such substantial disruption of LTR structure likely contributed to the substantial decreases in vector titer that have been observed with such vectors, since LTR structure is critical for efficient integration of the provirus into the cellular genome. By utilizing sequence alterations instead of deletions, the elimination of retroviral regulatory sequences with the maintenance of LTR structure and high titer are combined making the G2 vector series much more amenable to clinical applications where high titer is critical.

Figure 7:
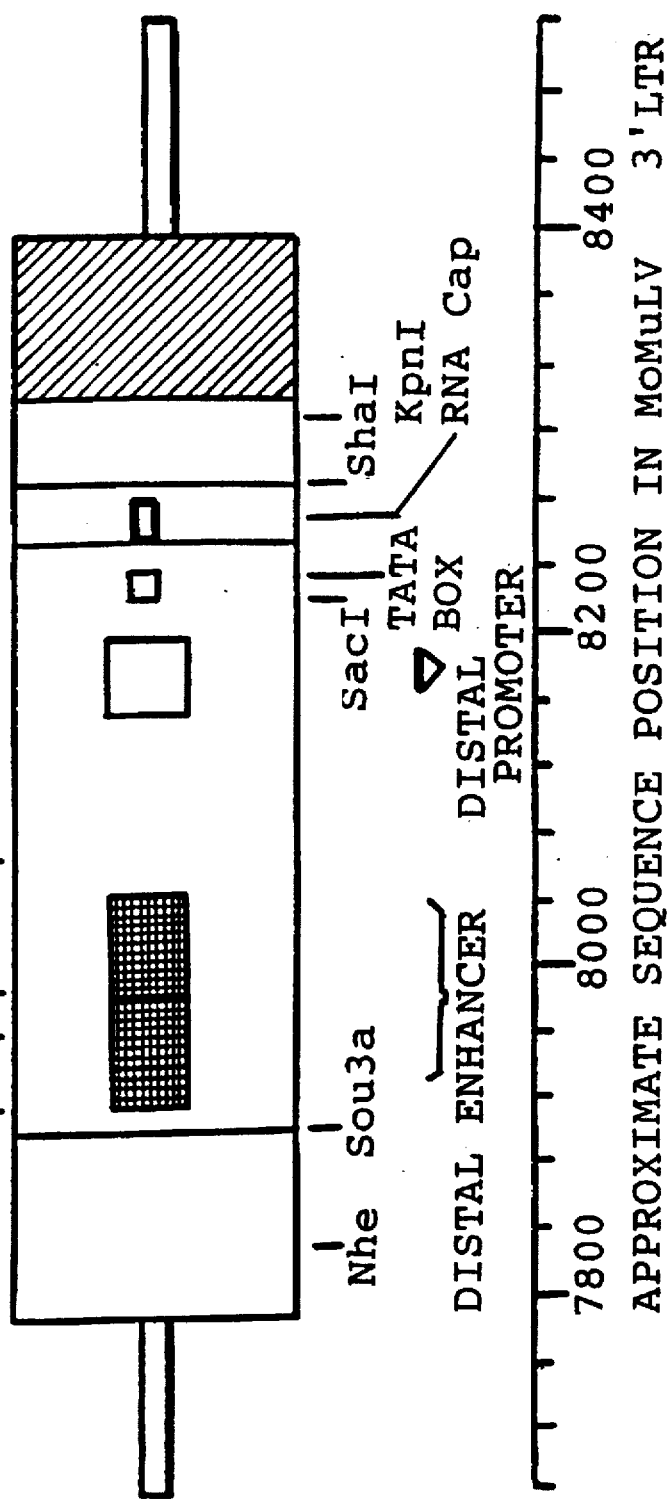
FIG. 7. Structure of the natural MoMuLV LTR and indicated region of altered sequence.

The details of the construction are as follows:

Starting with the pGO plasmid, we subcloned from this a 619 base pair ClaI/SmaI fragment from base pairs 7676 to 8295 of MoMuLV from the 3' end of env to just inside R. This fragment was further digested with Sau3A, and a 235 base pair ClaI/Sau3A fragment representing the 5' most portion, ending 12 base pairs 5' to the first long enhancer repeat within U3, was isolated. The remainder of the original ClaI/SmaI fragment was reconstructed with a series of twelve overlapping oligonucleotide fragments. These fragments maintained the overall length of the original LTR, but incorporated sequence alterations which eliminated the recognition sequences for enhancers or promoters. The overall result of this reconstruction was to generate a new ClaI/SmaI fragment equal in length and general structure to the native fragment, but with all enhancers, distal promoter and TATA regions altered to non-functionality. A diagram of the natural MoMuLV LTR and the region of the altered sequence is shown in FIG. 7. The altered sequence is shown in FIG. 8. This new ClaI/SmaI fragment was then restored into the remaining SmaI/ClaI fragment from pGO. Then, the same EcoRI fragment containing the 5' MoMuSV LTR as used to make pG1 was inserted into the unique EcoRI site of the altered pGO to yield the vector backbone pG2. This vector backbone is identical to pG1 up to the first Sau3A 3' of the unique ClaI site. Then, the 384 base pairs of the altered 3' LTR, and finally normal LTR sequence, including integration signals.

This vector combines all the cloning advantages of pG1, in that the multiple cloning site is compatible with that of the pGene plasmid. In addition, it incorporates changes, but not deletions, of the 3' LTR such that inactivation of retroviral regulatory sequences occurs in the integrated provirus without sacrifice of integration efficiency and its reflection in maintenance of high titer. The pG2 vector provides a useful backbone for the introduction and expression of genes which require regulation of maximal accuracy. This enables one to correct genetic defects involving genes under very precise physiological regulation.

EXAMPLE 3

Figure 9:
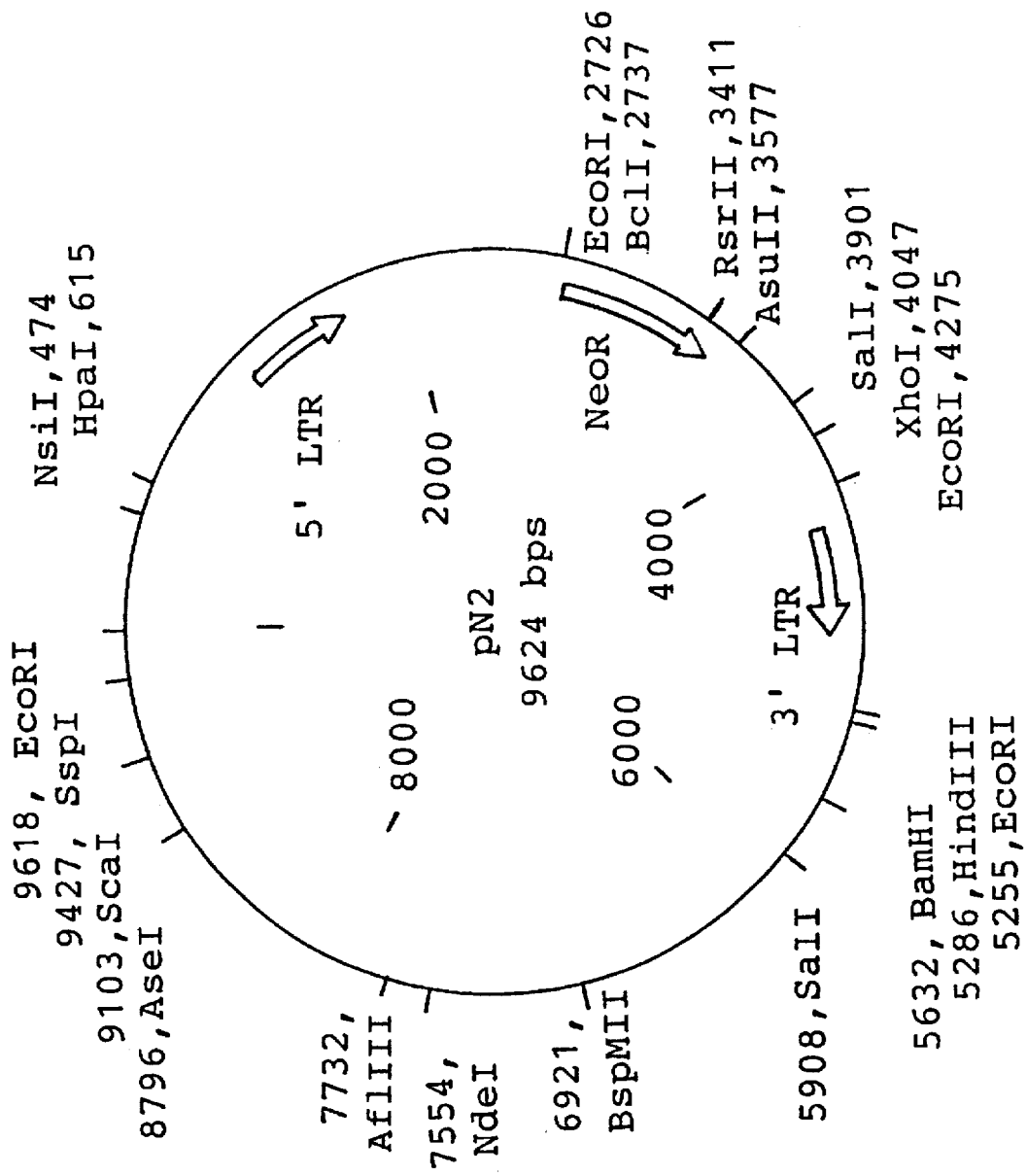
FIG. 9. Map of plasmid pN2.
Figure 10:
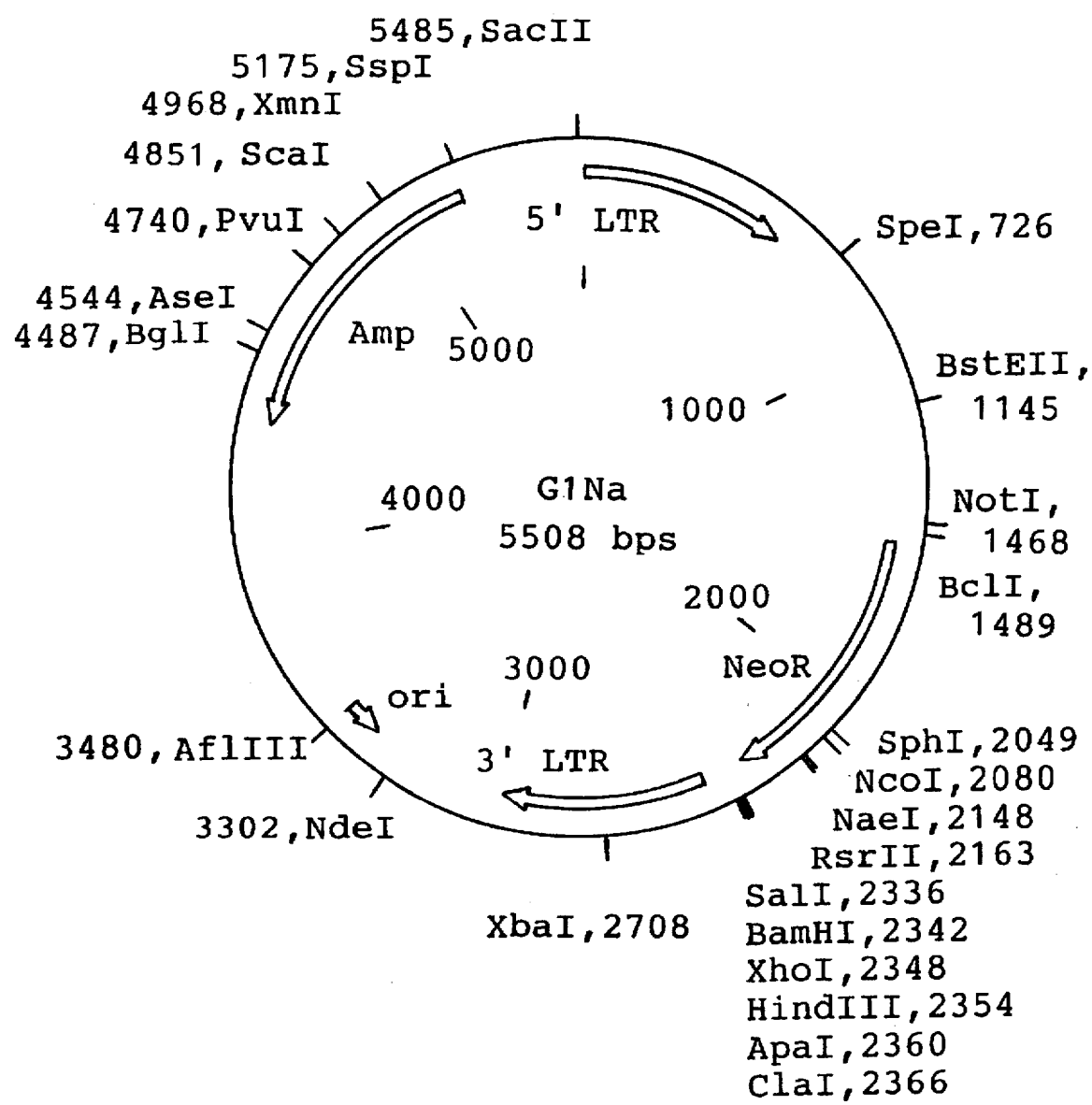
FIG. 10. Map of plasmid G1Na.
Figure 11:
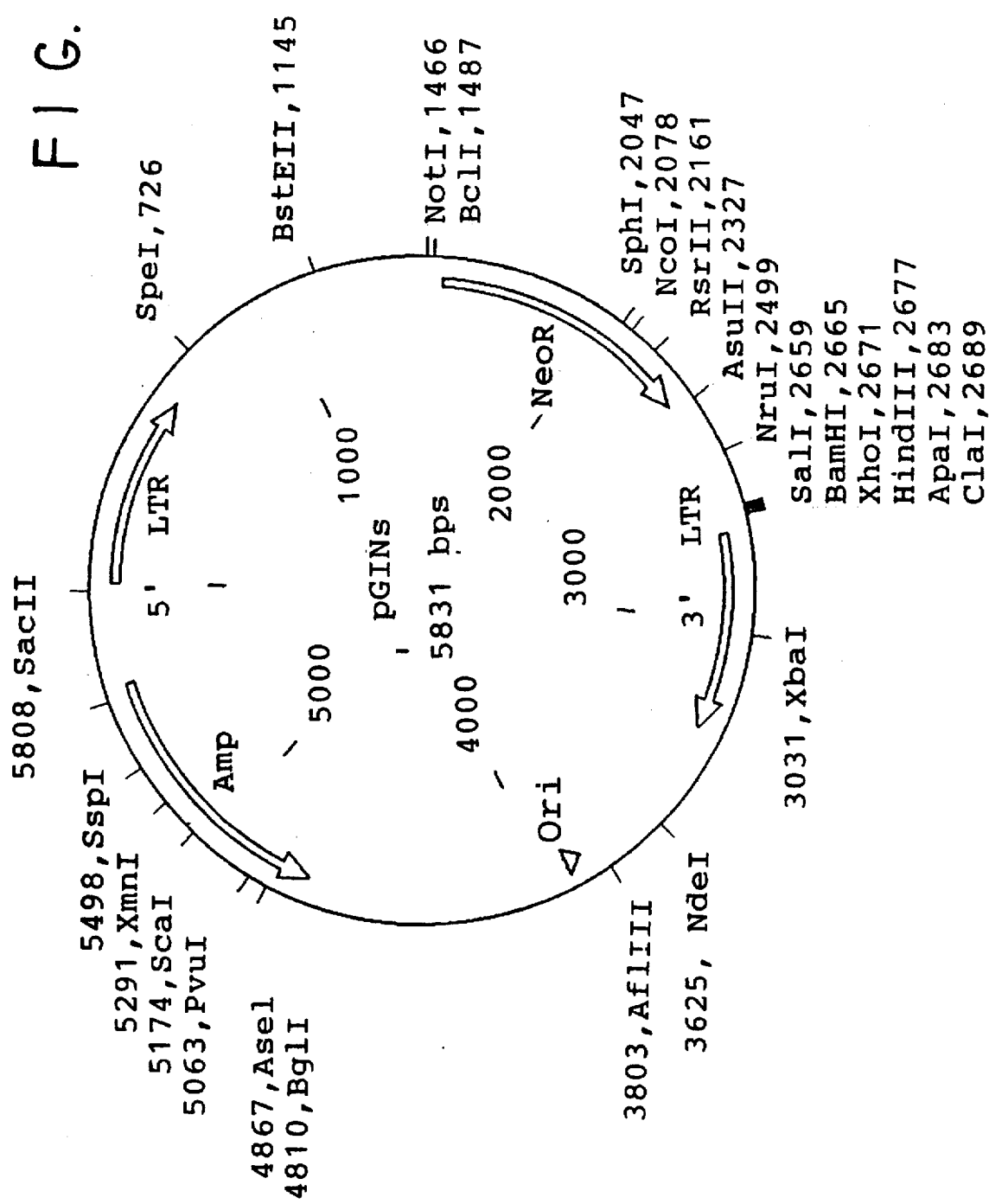
FIG. 11. Map of plasmid pG1Ns.

The "backbone" vectors pG1Na and pG1Ns were constructed from pG1 and pN2 (Armentano, et al., *J. Virology,* Vol. 61, pgs. 1647–1650 (1987)). pG1Na was constructed by cutting pN2 (FIG. 9) with EcoRI and AsuII, filling in the ends of the EcoRI/AsuII fragment containing the neo$^R$ gene, and ligating the fragment into SnaBI digested pG1 to form pG1Na (FIG. 10). pG1Ns was constructed by cutting pN2 with EcoRI and SalI, filling in the ends of the EcoRI/SalI fragment containing the neo$^R$ gene, and ligating the fragment into SnaBI digested pG1, thereby forming pG1Ns (FIG. 11).

EXAMPLE 4

In this as well as in following examples, the following abbreviations are used for genes and promoters:

Human TNFα

T11: leader, Kozak, and rat growth hormone secretion signal created by oligomers; mature coding sequence from Beckman T12: leader, Kozak, and TNFa secretion signal created by oligomers; mature coding sequence from Beckman T2: leader and Kozak; PCR-generated (from RNA) full coding sequence Human IFNα

F1: IFNα$_2$: leader, Kozak, and IFNα$_2$ secretion signal; IFNα$_2$ mature coding region from Hoffman-LaRoche F2: IFNαA/D: leader, Kozak, and IFNα secretion signal; chimeric IFNαA/IFNα$_D$ mature coding region from Hoffman-LaRoche Human IFN F31: Kozak region only (no leader); PCR-generated coding region (from RNA)

F32: leader and Kozak; PCR-generated coding region (from RNA)

Human IL-1β i11: leader, Kozak and rat growth hormone secretion signal created by oligomers; mature coding sequence from Beckman I2: leader, Kozak and IL-1β secretion signal created by oligomers; mature coding sequence from Beckman Human IL-2

I2: leader, Kozak, and IL-2 secretion signal added by oligomers; mature coding sequence from ATCC; 3' untranslated region removed I2G: leader, Kozak; PCR-generated full coding sequence using Roche IL-2 gene as template Human IL-2 Receptor I2Rα: IL-2Rα5'-untranslated region, coding region, and 3'-untranslated region I2Rβ:IL-2Rβ5'-untranslated region, coding region, and 3'-untranslated region Human IL-4

I4: leader and Kozak; PCR-generated full coding region from ATCC template

Mouse IL-4 mI41: mouse IL-4 5'-untranslated region and coding region from ATCC; 3'-untranslated region removed mI42: leader and Kozak; PCR-generated full coding region from ATCC template Human GM-CSF Gm: leader and Kozak; PCR-generated full coding region from MO T-lymphocyte RNA Human ADA AD: Gilboa, et al., *Biotechniques,* Vol. 4, pgs. 504–512, (1986)

Promoters

Bc: chicken β-actin promoter

βh: human β-actin promoter

B19: parvovirus B19 promoter

Cv: CMV (cytomegalovirus) promoter

I2: IL-2 promoter

I2R: IL-2 receptorα promoter

Sv: SV40 promoter

As shown in Table I below, pG1Na was cut at various restriction enzyme sites, and restriction fragments containing various genes and/or promoters were ligated into the cut pG1Na to form retroviral vector products containing the desired genes and/or promoters as listed in Table I below.

TABLE I

| Sites cut in pG1Na | Fragment | Product |
|---|---|---|
| SalI/ClaI | SalI-Cvil2-ClaI | pG1NaCvil2 |
| SalI/ClaI | SalI-Svil2-ClaI | pG1NaSvil2 |
| SalI/BamHI | XbaI-Bc-BamHI | pG1NaBcX |
| SalI/BamHI | XbaI-B19-BamHI | pG1NaB19X |

Figure 12:
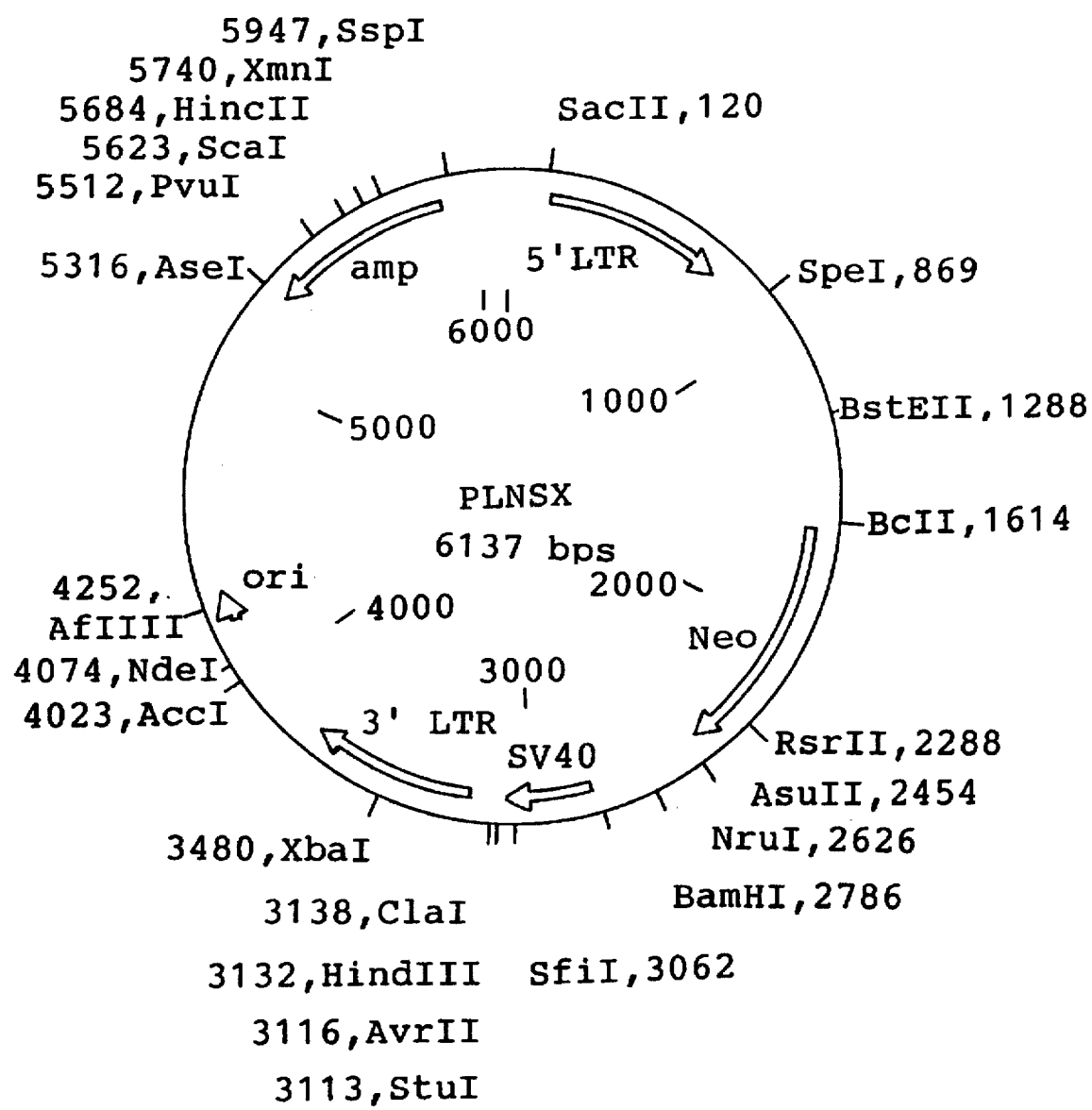
FIG. 12. Map of plasmid pLNSX.
Figure 13:
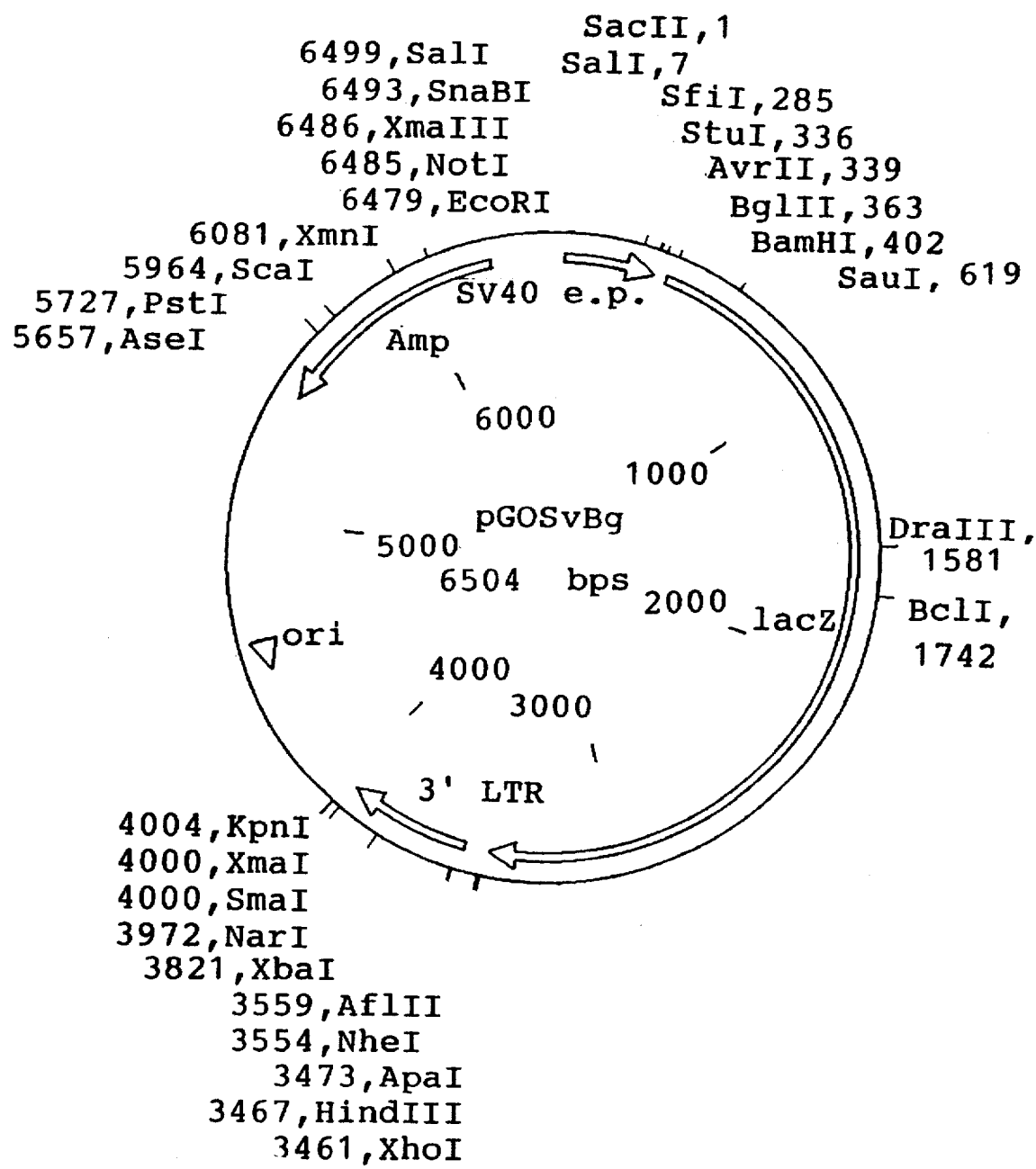
FIG. 13. Map of plasmid pGOSvBg.
Figure 14:
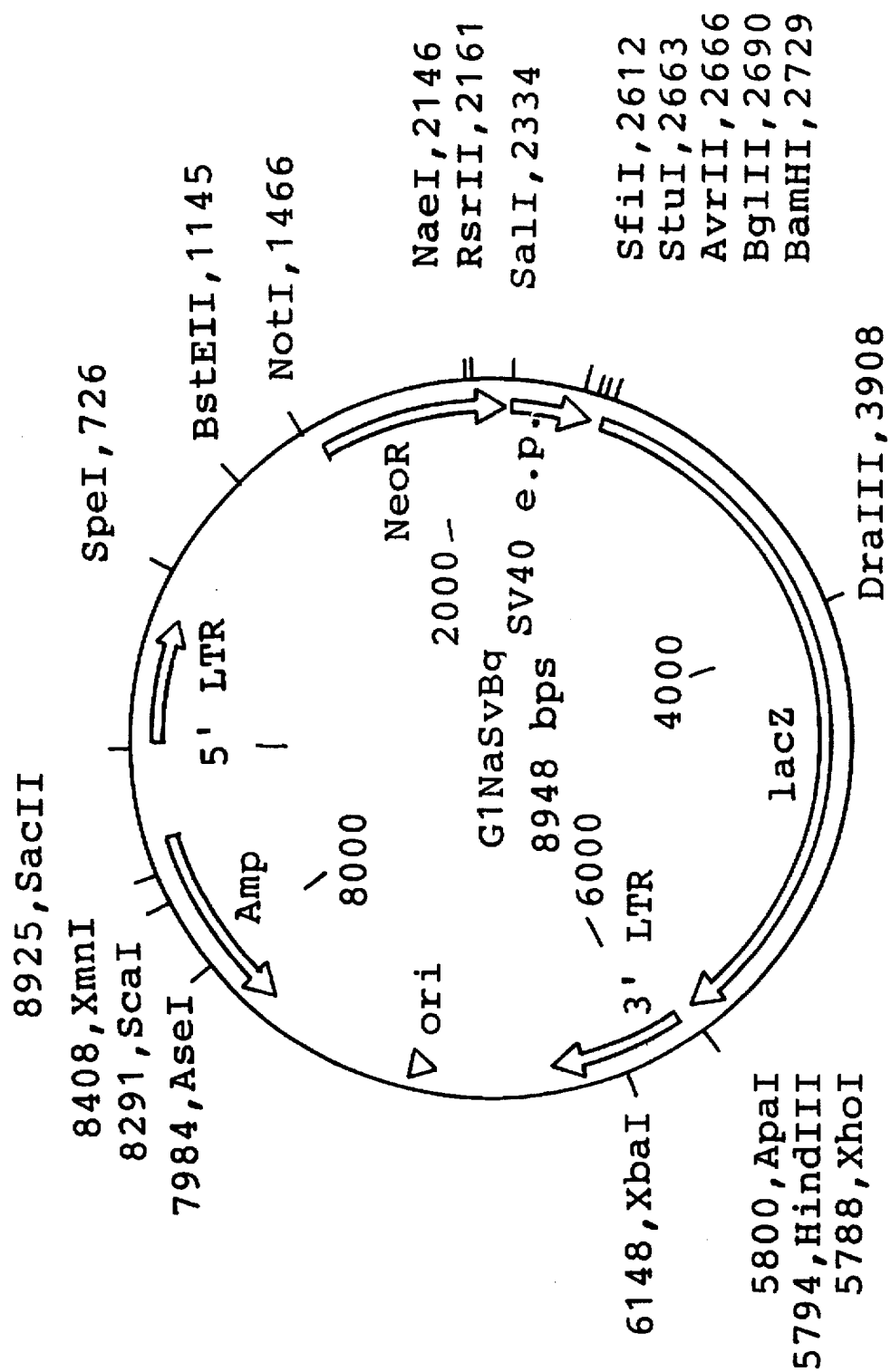
FIG. 14. Map of plasmid pG1NaScBg.

EXAMPLE 5 pG1Na was cut with SalI and XhoI. pBg was cut with NruI and XhoI, and an NruI/XhoI fragment containing the lac Z gene of pBg was cloned into the SnaBI site of pGO. Also cloned into pGO 5' to the lac Z gene was a BamHI-HindIII fragment containing the SV40 promoter from pLNSX (FIG. 12). The resulting plasmid is pGOSvBg (FIG. 13). pGOSvBg was then cut with SalI and XhoI, and a SalI-XhoI fragment containing an SV40 promoter and a β-galactosidase gene was ligated into the SalI/XhoI digested pG1Na to form pG1NaSvBg. (FIG. 14).

pG1NaSvBg was cut at various restriction enzyme sites, and restriction fragments containing various genes were ligated into the cut pg1NaSvBg to form retroviral vector products containing the desired genes as listed in Table II below.

TABLE II

| Sites Cut in pG1NaSvBg | Fragment | Product |
|---|---|---|
| BglII/XhoI | BglII-T2-XhoI | pG1NaSvT2 |
| BglII/HindIII | BglII-I2G-HindIII | pG1NaSvI2G |
| BglII/ClaI (end-filled) | EcoRI-I2Rα-EcoRI (end-filled) | pG1NaSvI2Rα |
| BglII/ClaI (end-filled) | EcoRI-I2Rβ-EcoRI (end-filled) | pG1NaSvI2Rβ |
| BglII/ClaI (end-filled) | BamHI-mI41-ScaI (end-filled) | pG1NaSvmi41 |
| BglII/HindIII | BglII-mI42-HindIII | pG1NaSvmi42 |
| BglII/ClaI | BglII-I4-ClaI | pG1NaSvI4 |

Figure 15:
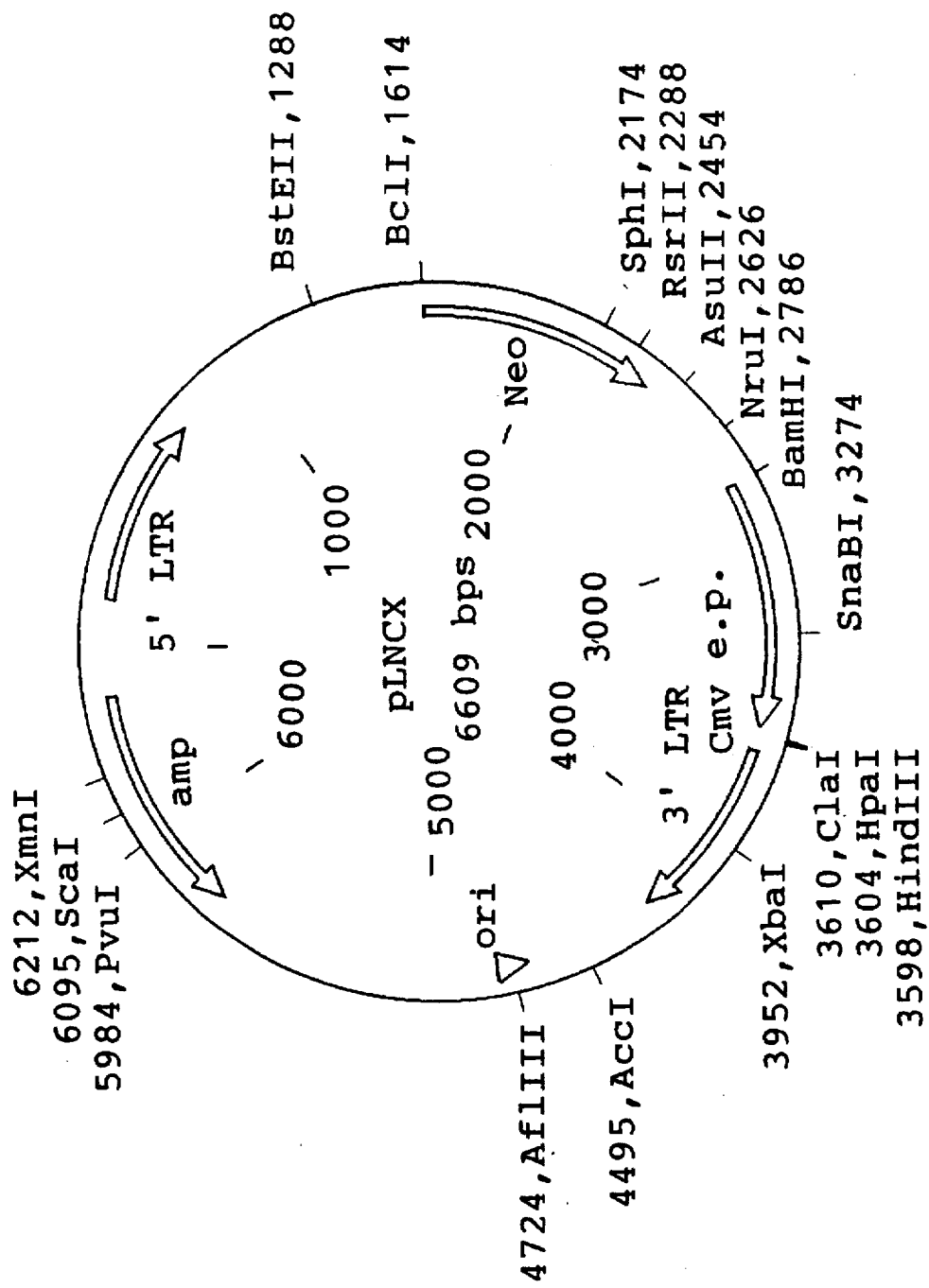
FIG. 15. Map of plasmid pLNCX.
Figure 16:
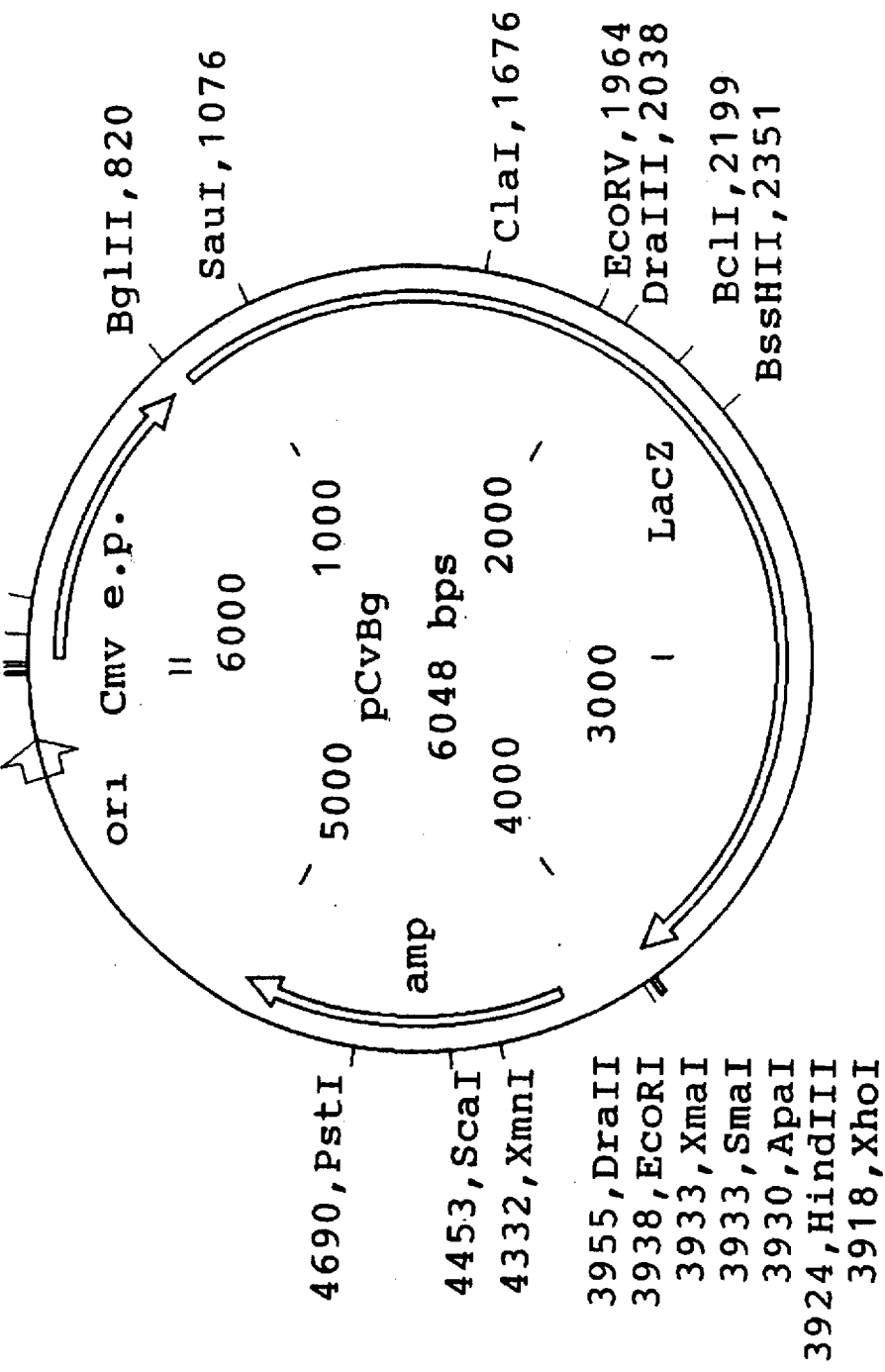
FIG. 16. Map of plasmid pCvBg.
Figure 17:
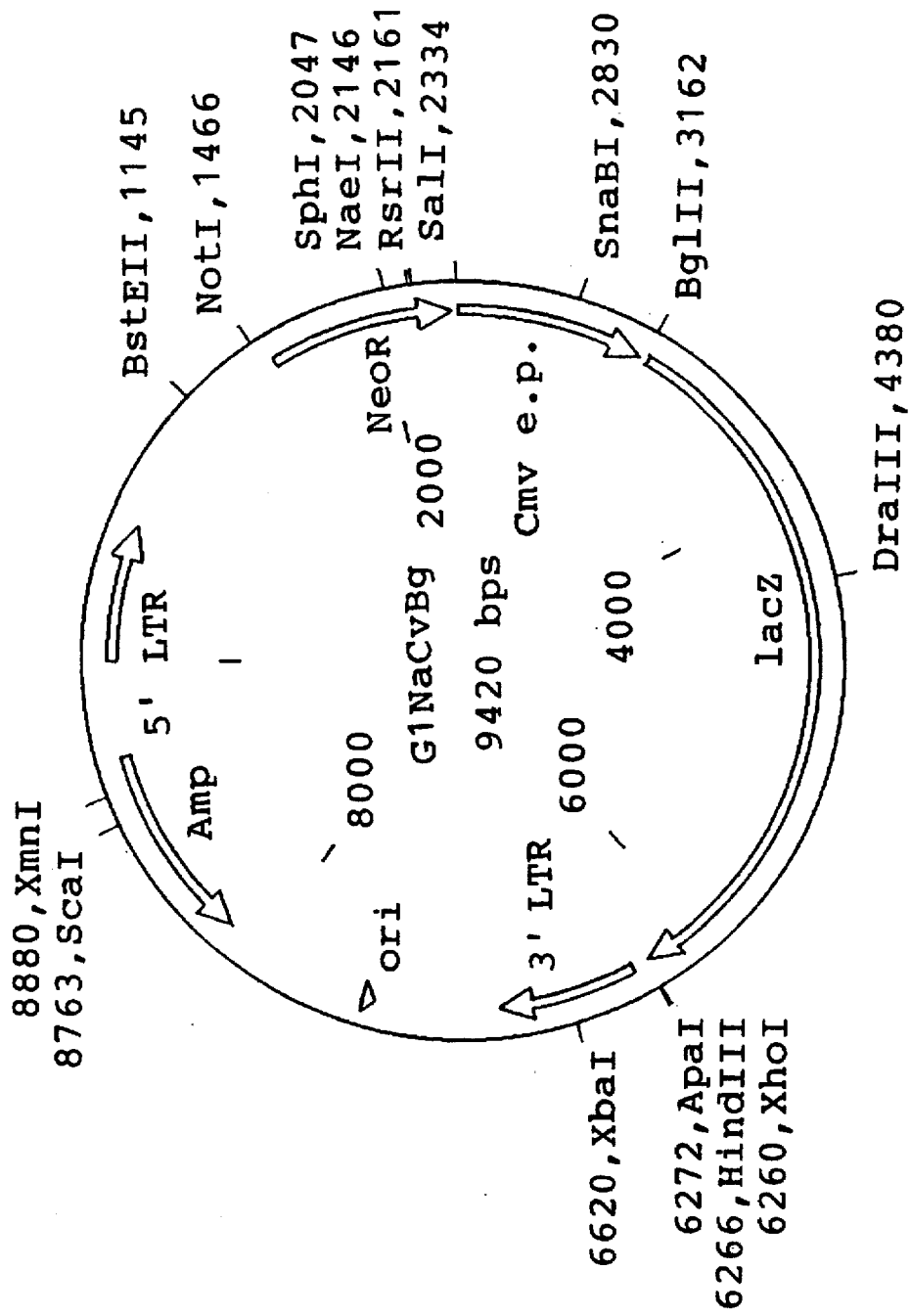
FIG. 17. Map of plasmid pG1NaCvBg.

EXAMPLE 6 pG1Na was cut with SalI and XhoI. A BamHI-HindIII fragment of pLNCX (FIG. 15) is cloned into the SnaBI site of pBg to form pCvBg (FIG. 16). pCvBg was then cut with SalI and XhoI, and a SalI-XhoI fragment containing a cytomegalovirus (CMV) promoter and a β-galactosidase gene was ligated into the SalI/XhoI digested pG1Na to form pG1NaCvBg (FIG. 17).

pG1NaCvBg was cut at various restriction enzyme sites, and restriction fragments containing various genes were ligated into the cut pG1NaCvBg to form retroviral vector products containing the desired genes as listed in Table III below.

TABLE III

| Sites cut in pG1NaCvBg | Fragment | Product |
|---|---|---|
| BglII/XhoI | BglII-T2-XhoI | pG1NaCvT2 |
| BglII/HindIII | BglII-I2G-HindIII | pG1NaCvI2G |
| BglII/XhoI | BglII-F32-XhoI | pG1NaCvF32 |

Figure 18:
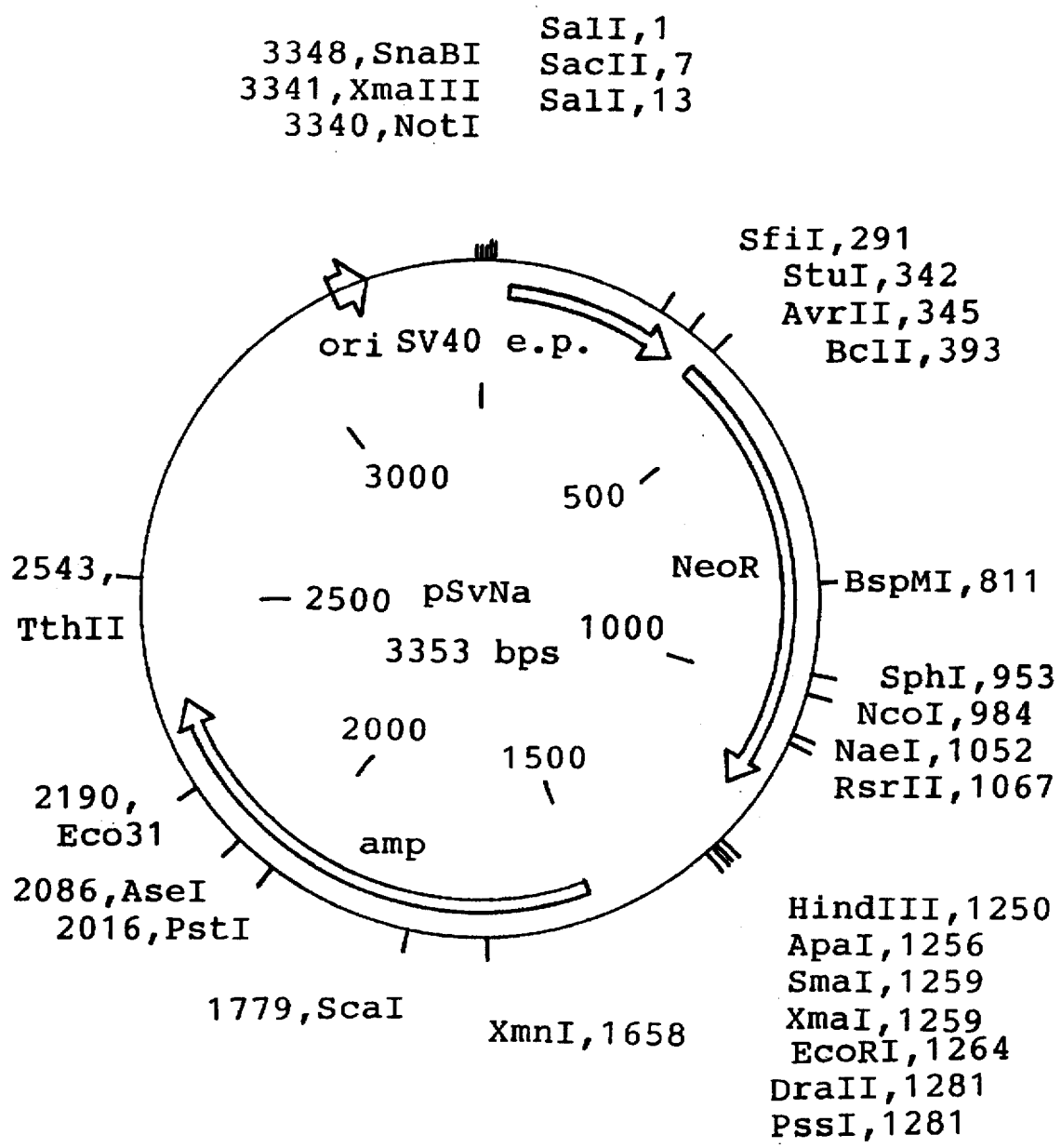
FIG. 18. Map of plasmid pSvNa.
Figure 19:
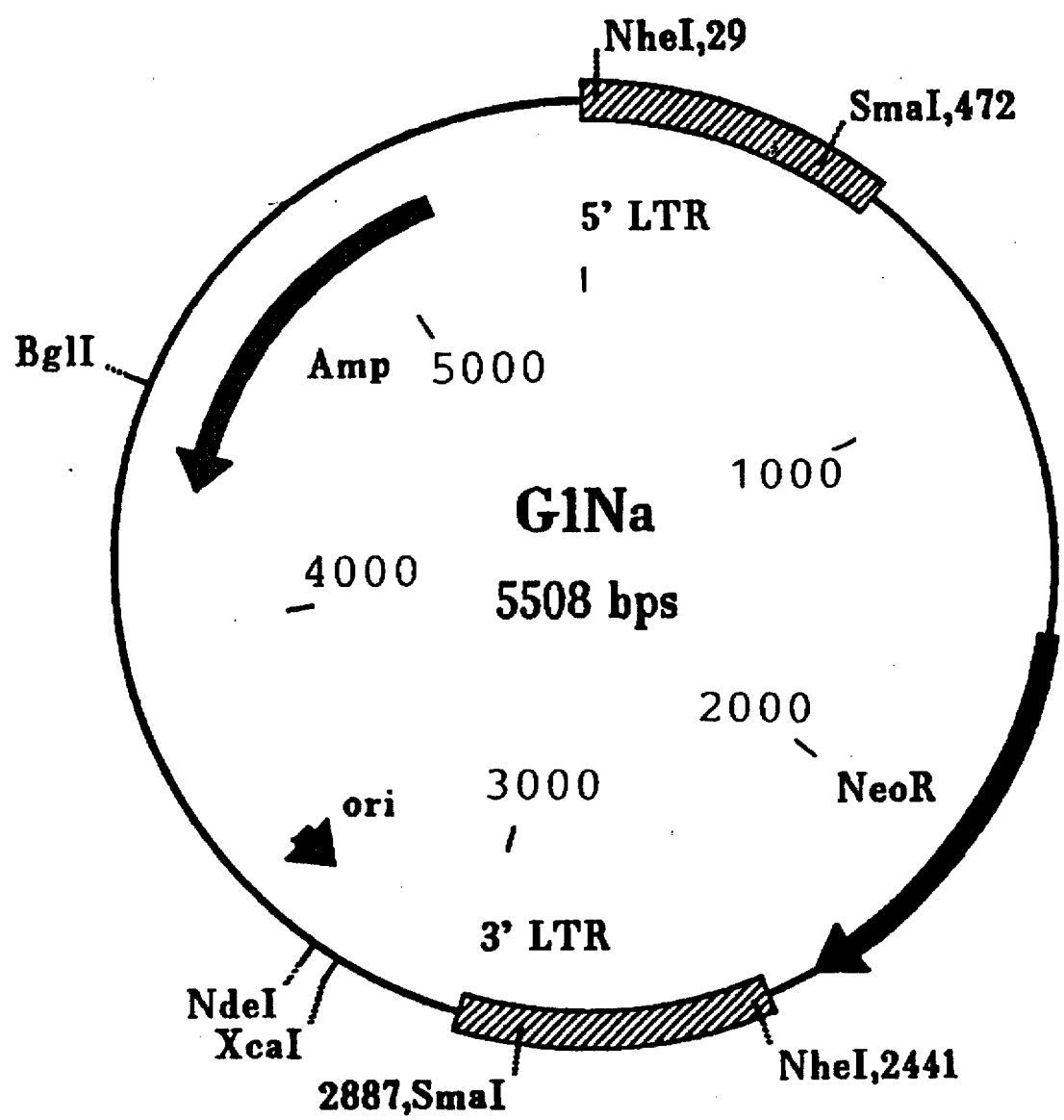
FIG. 19. Map of plasmid pG1XSvNa.

EXAMPLE 7 pG1 was cut with HindIII and SalI. pSvNa (FIG. 18), which contains the SV40 promoter from pLNSX and the neo$^R$gene from pN2, was also cut with HindIII and SalI, and a HindIII-SalI fragment containing an SV40 promoter and a β-galactosidase gene was ligated into HindIII/SalI digested pG1 to form pG1XSvNa (FIG. 19).

pG1XSvNa was then cut at various restriction enzyme sites, and restriction fragments containing various genes were ligated into the cut pG1XSvNa to form retroviral vector products containing the desired genes as listed in Table IV below.

TABLE IV

| Sites cut in pG1XSvNa | Fragment | Product |
|---|---|---|
| SnaBI/SalI | blunt BglII-T2-XhoI | pG1T2SvNa |
| SnaBI | BglII-i12-BamHI (end-filled) | pG1i12SvNa |
| SnaBI | BglII-I2-ClaI (end-filled) | pG1I2SvNa |
| SnaBI | BglII-I2G-HindIII (end-filled) | pG1I2GSvNa |
| SnaBI | EcoRI-I2Rα-EcoRI (end-filled) | pG1I2RαSvNa |
| SnaBI | EcoRI-I2Rβ-EcoRI (end-filled) | pG1I2RβSvNa |
| SnaBI | BamHI-ml41-ScaI (end-filled) | pG1ml41SvNa |
| SnaBI | BglII-ml42-HindIII (end-filled) | pG1ml42SvNa |
| SnaBI | BglII-I4-ClaI (end-filled) | pG1I4SvNa |
| SnaBI | SnaBI-F1-DraI | pG1F1SvNa |
| SnaBI | SnaBI-F2-EcoRI (end-filled) | pG1F2SvNa |
| SnaBI/SalI | SnaBI-F31-SalI | pG1F31SvNa |
| NotI/StuI | NotI-T12-StuI | pG1T12SvNa |
| NotI/StuI | NotI-T11-StuI | pG1T11SvNa |

Figure 20:
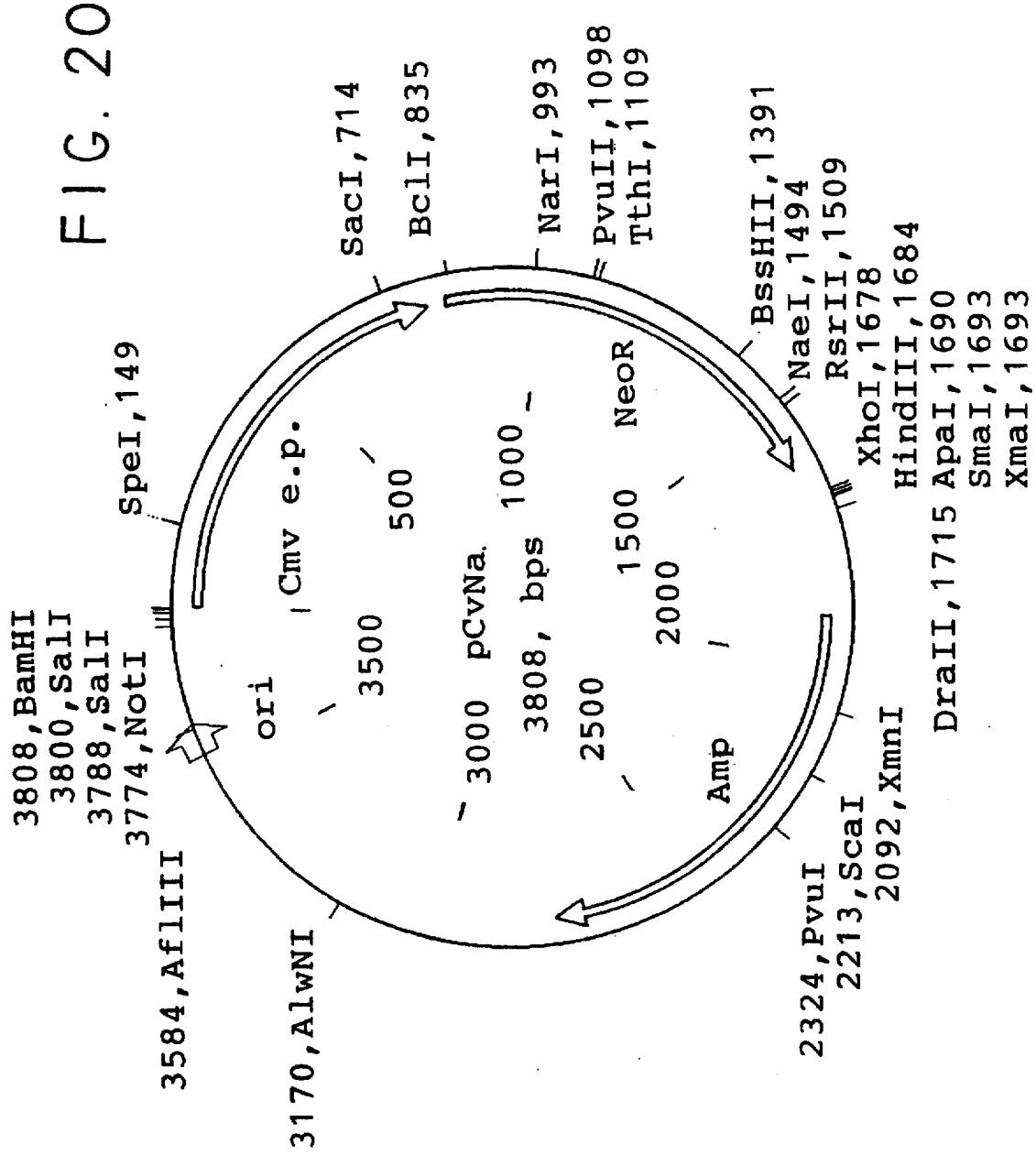
FIG. 20. Map of plasmid pCvNa.
Figure 21:
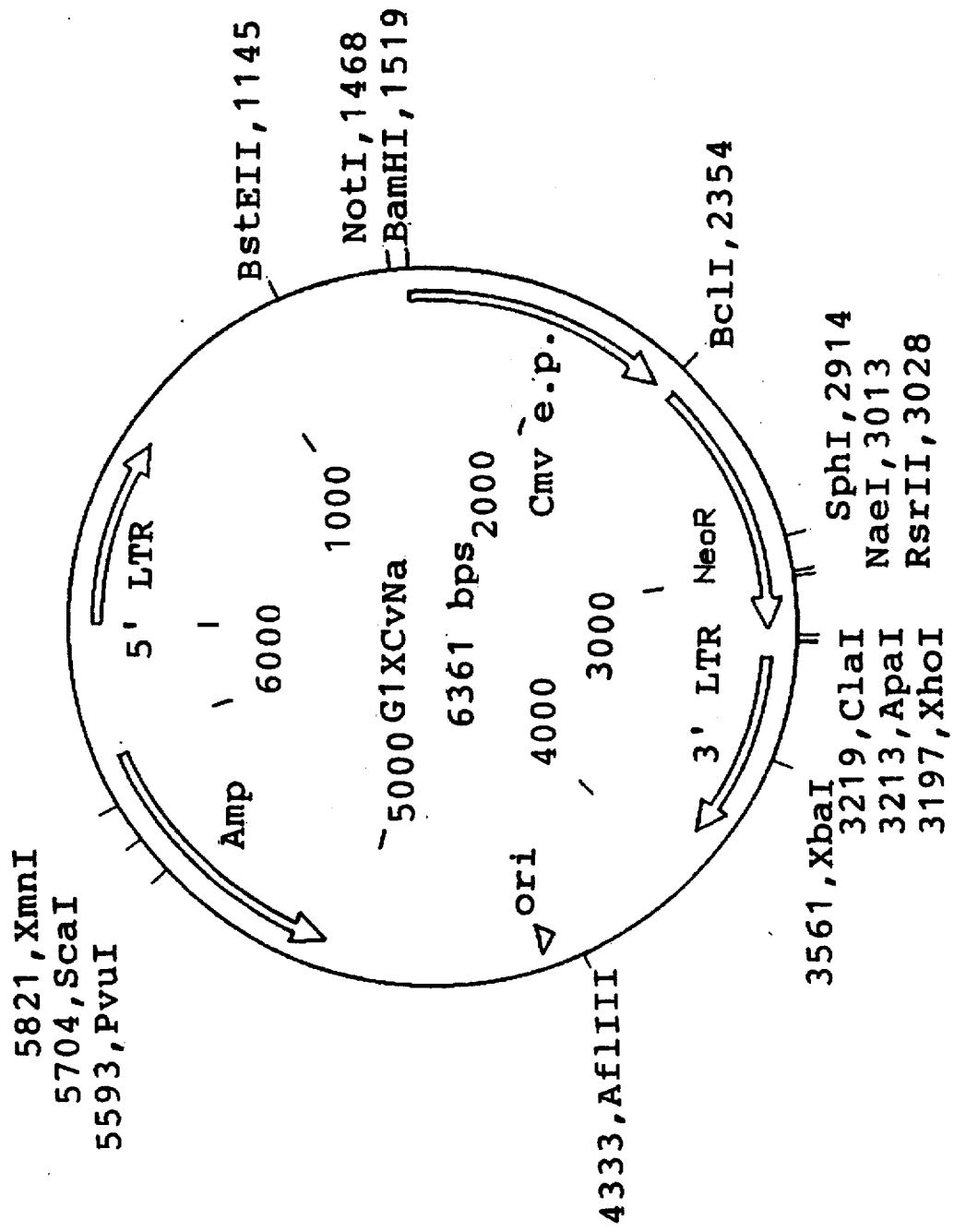
FIG. 21. Map of plasmid pG1XCvNa.

EXAMPLE 8 pG1 was cut with HindIII and SalI. pCvNa (FIG. 20), which contains the CMV promoter from pLNCX and the neo$^R$gene from pN2, was then cut with HindIII and SalI, and a HindIII-SalI fragment containing a cytomegalovirus promoter and a neo$^R$gene was ligated to HindIII/SalI digested pG1 to form pG1XCvNa. (FIG. 21).

Figure 22:
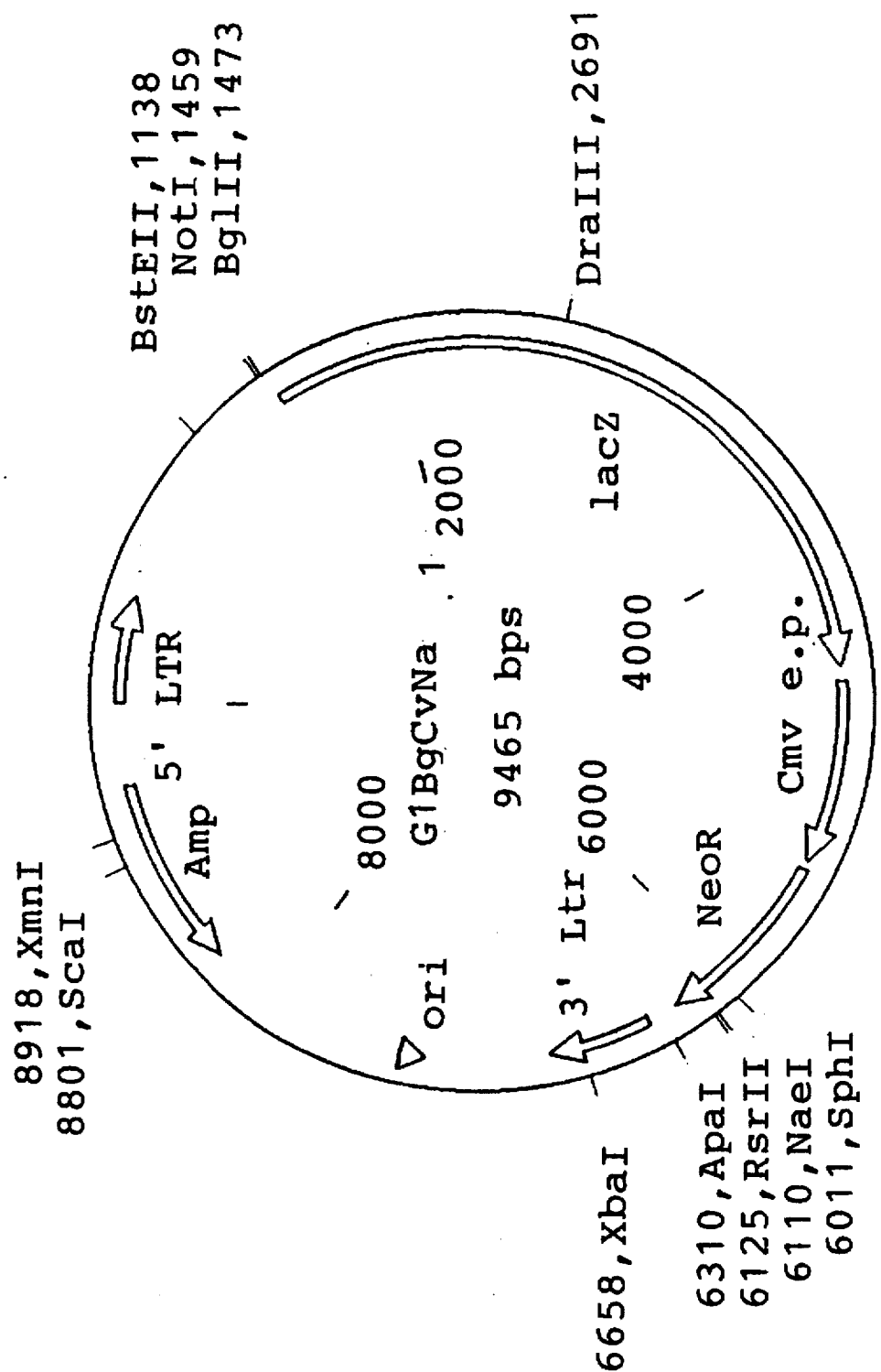
FIG. 22. Map of plasmid pG1BgCvNa.

EXAMPLE 9 pG1Bg (constructed as described in Example 1) was cut with SalI and HindIII. Each of pCvNa and pSvNa were also cut with SalI and HindIII, and SalI-HindIII fragments containing (i) a CMV promoter and a neo$^R$gene, or (ii) an SV40 promoter and a neo$^R$gene were ligated to the SalI/HindIII digested pG1Bg to form pG1BgCvNa (FIG. 22) and pG1BgSvNa (FIG. 23), respectively.

Figure 24:
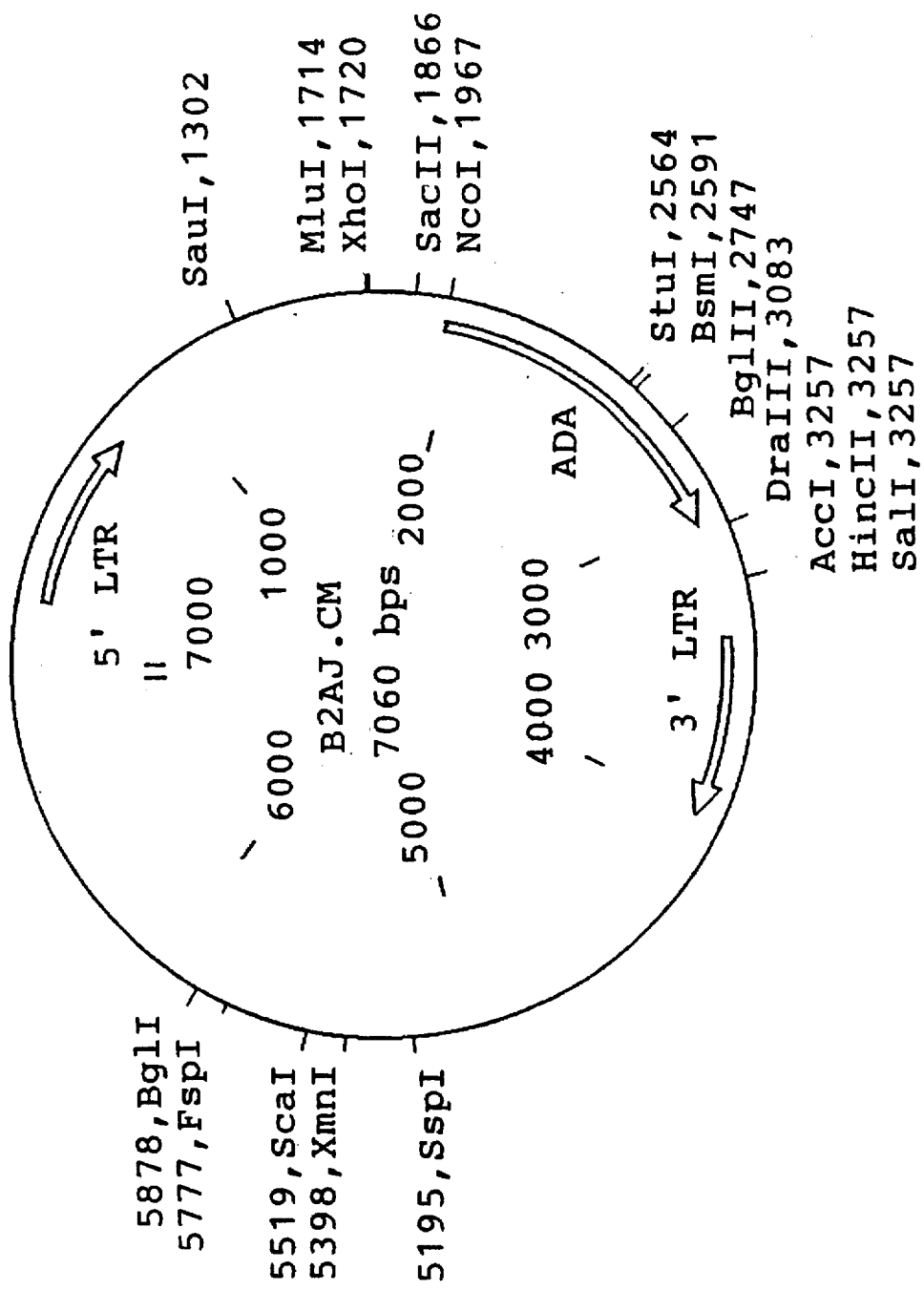
FIG. 24. Map of plasmid pB2AJ.
Figure 25:
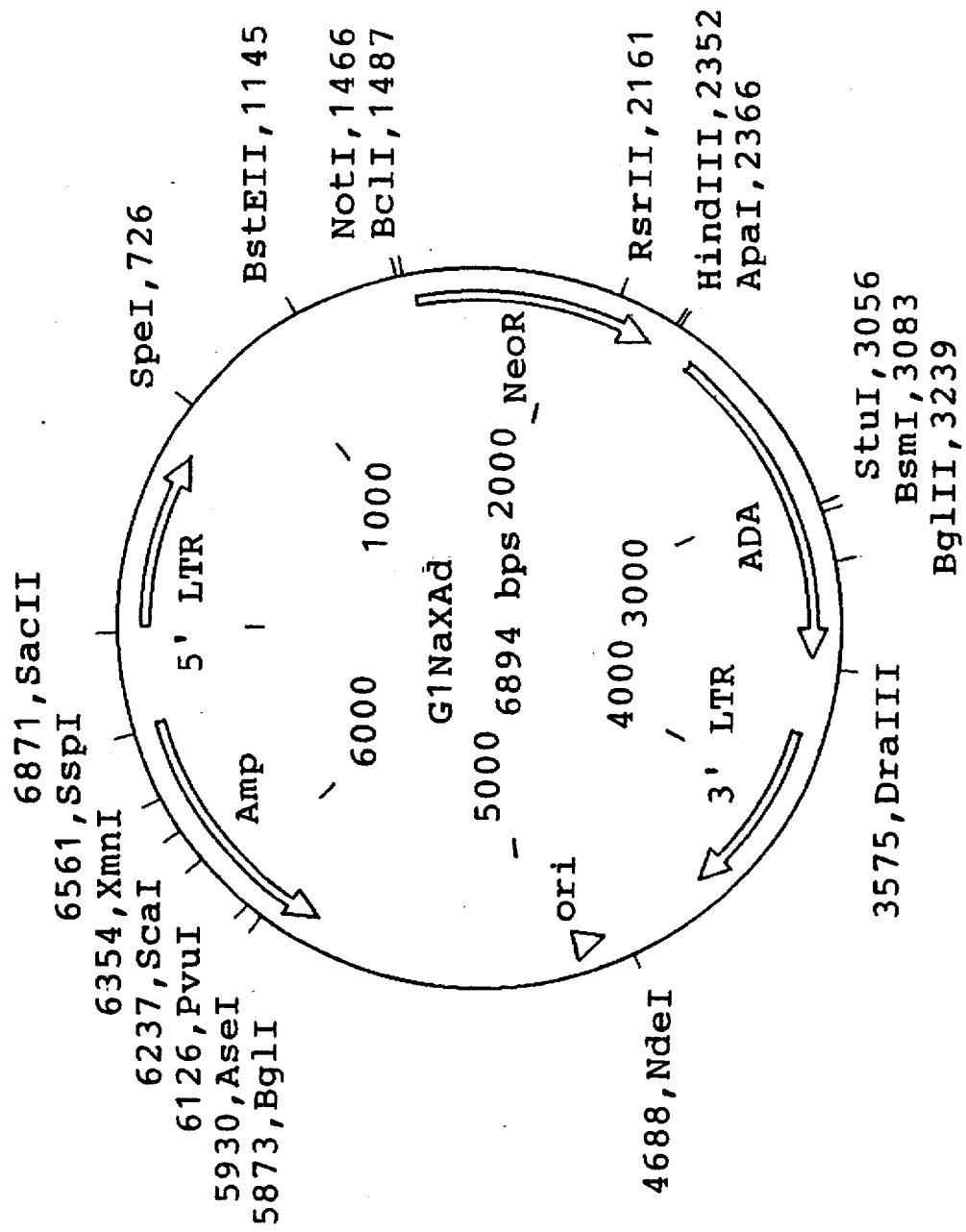
FIG. 25. Map of plasmid pG1NaXAd.

EXAMPLE 10 pG1Na was digested with ClaI, and the ends were filled in with Klenow. pB2AJ (FIG. 24), which is a modified pB2 plasmid (Zwiebel, et al., Science, Vol. 243, pg. 220 (1989), which contains a human ADA gene, is cut with SalI and XhoI and the ends are filled in with Klenow. An end-filled SalI-XhoI fragment containing the human ADA gene is ligated to the ClaI-digested and end-filled pG1Na to form pG1NaXAD. (FIG. 25).

pG1NaXAD was cut at various restriction enzyme sites, and restriction fragments containing various genes or promoters were ligated into the cut pG1NaXAD to form retroviral vector products containing the desired genes or promoters as listed in Table V below.

TABLE V

| Sites cut in pG1NaXAD | Fragment | Product |
|---|---|---|
| XhoI | XhoI-B19-SalI | pG1NaB19AD |
| HindIII | HindIII-I2-HindIII | pG1NaI2AD |
| HindIII | HindIII-I2R-HindIII | pG1NaI2RAD |

EXAMPLE 11

Figure 26:
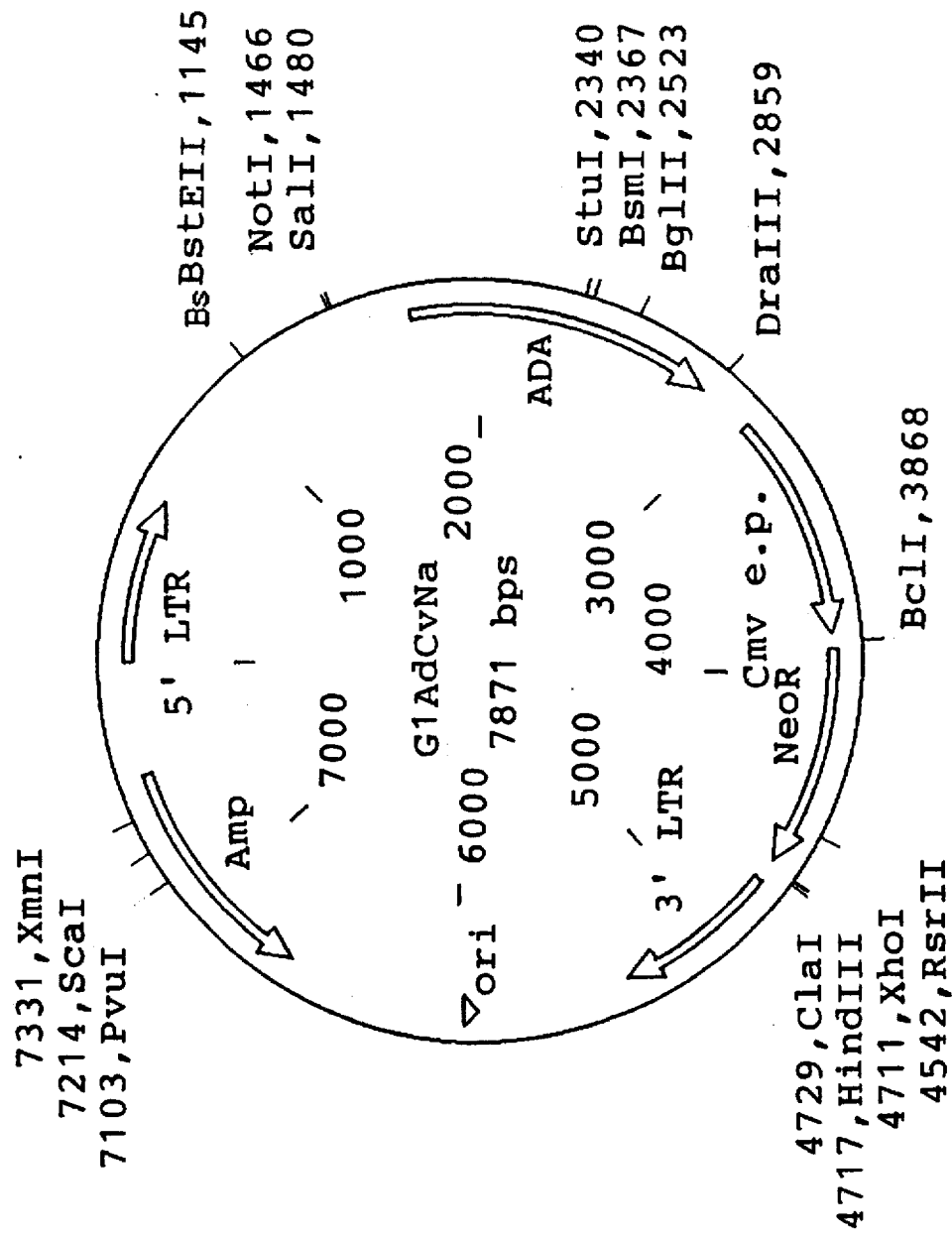
FIG. 26. Map of plasmid pG1AdCvNa.
Figure 27:
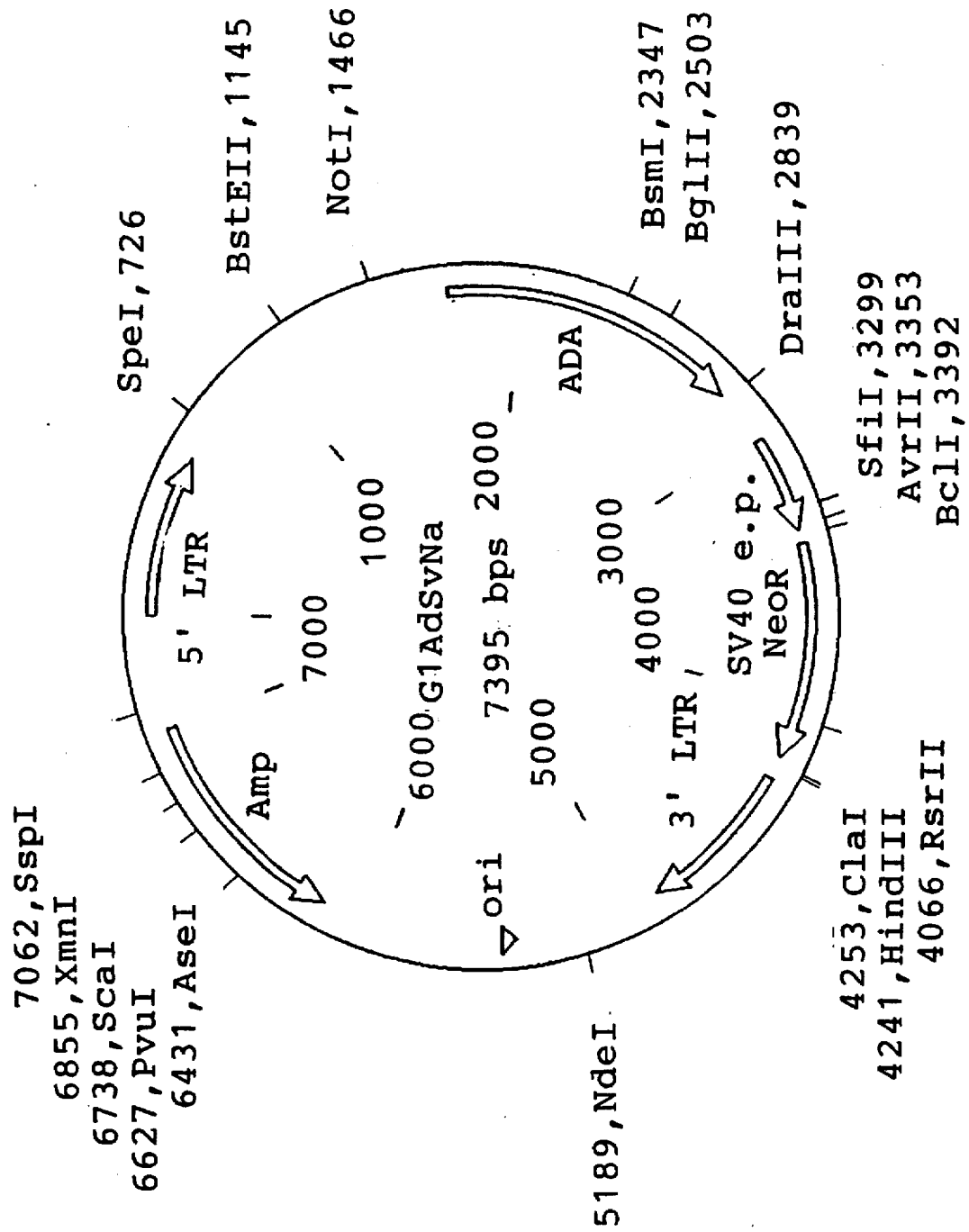
FIG. 27. Map of plasmid pG1AdSvNa.

Each of pG1XCvNa and pG1XSvNa is cut with SalI and XhoI. pB2AJ is cut with SalI and XhoI. A SalI-XhoI fragment from pB2AJ containing the human ADA gene is ligated into SalI/XhoI digested pG1XCvNa or pG1XSvNa to form pG1ADCvNa (FIG. 26) and pG1ADSvNa (FIG. 27), respectively.

Figure 28:
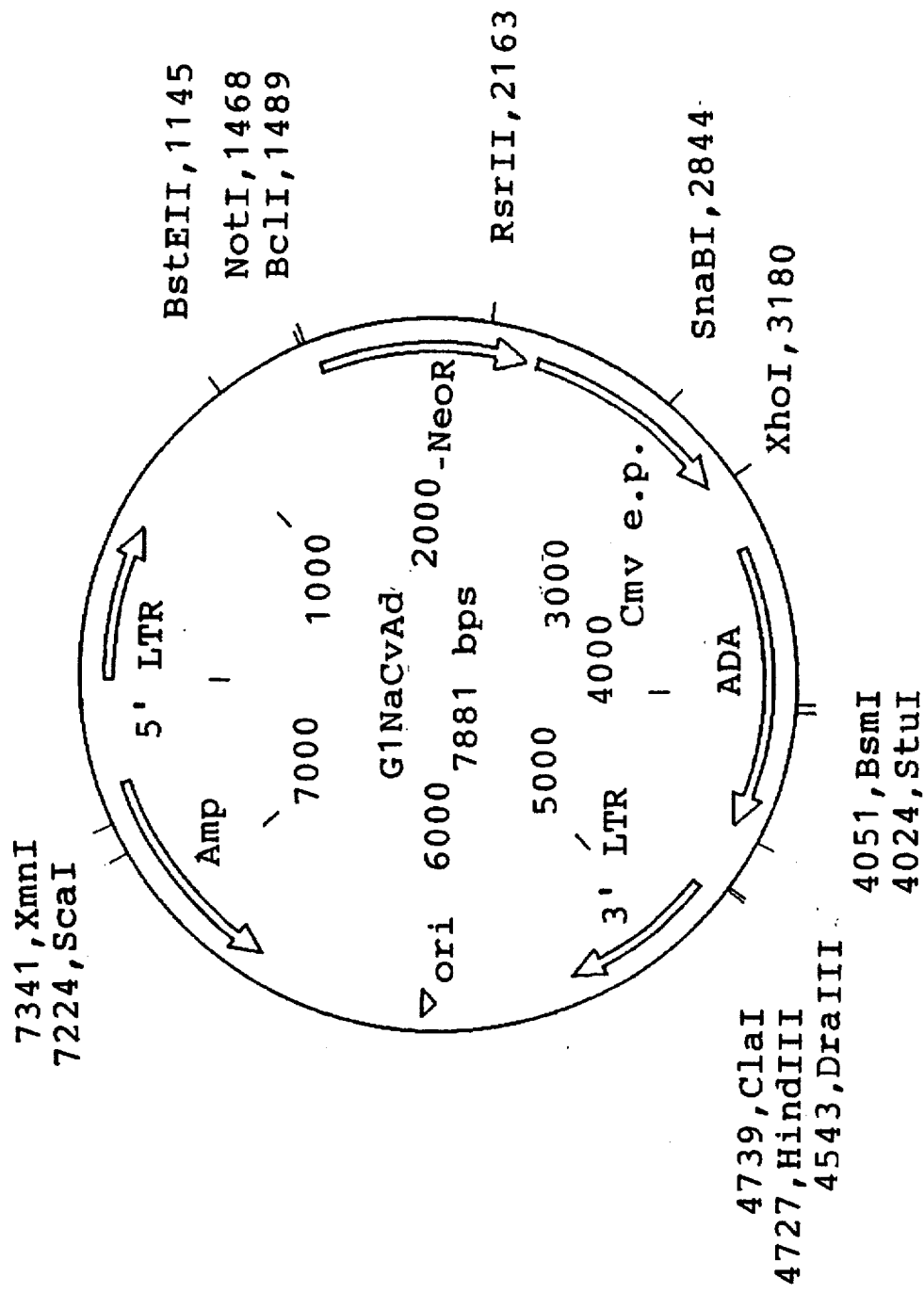
FIG. 28. Map of plasmid pG1NaCvAd.

EXAMPLE 12 pG1NaCvBg is cut with BglII and ClaI, and the ends are filled in with Klenow. pB2AJ is cut with SalI and XhoI and the ends are filled in with Klenow. An end-filled SalI-XhoI fragment from pB2AJ containing the human ADA gene is ligated to the end-filled BglII/ClaI digested pG1NaCvBg to form pG1NaCvAD (FIG. 28).

Figure 29:
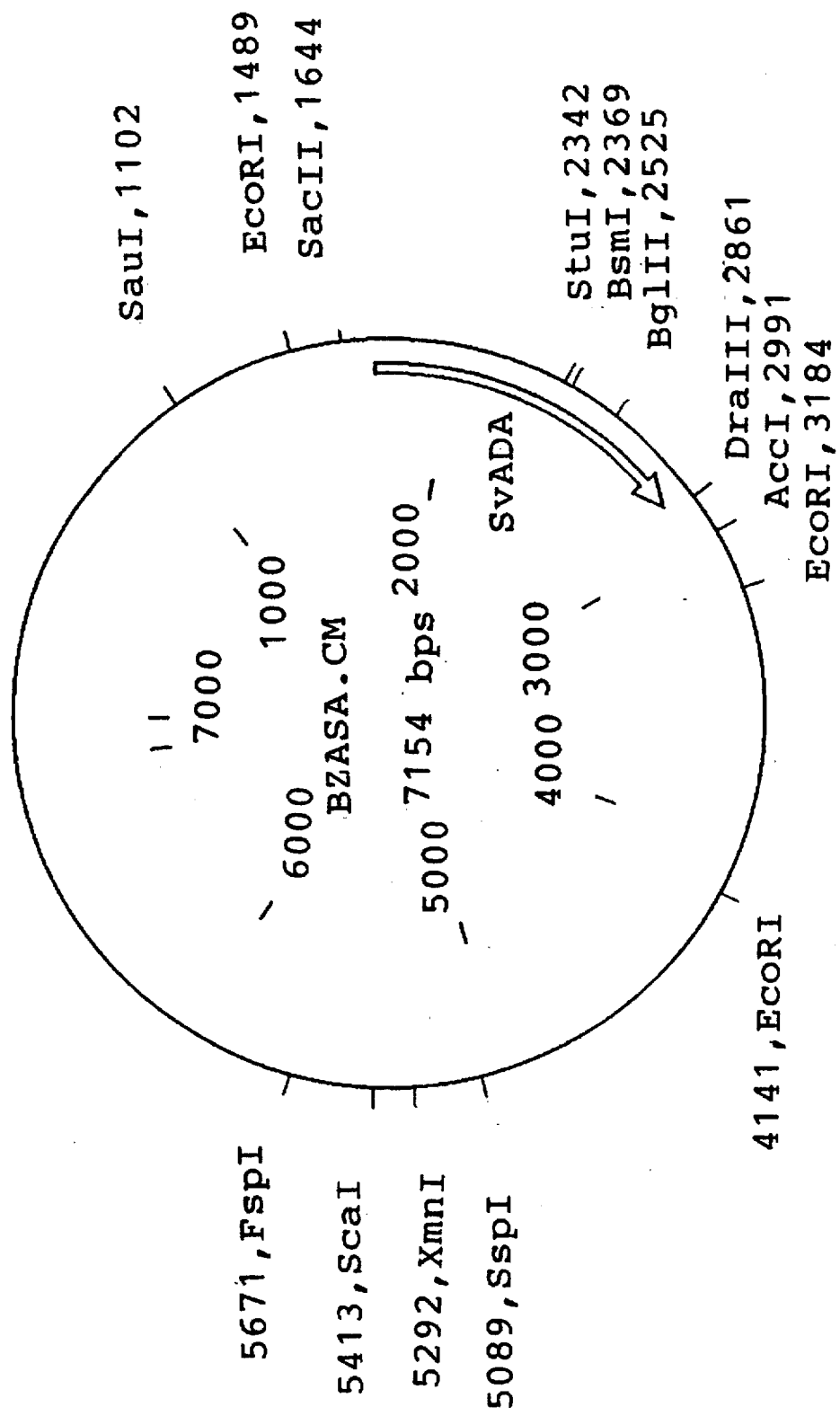
FIG. 29. Map of plasmid pB2ASA.
Figure 30:
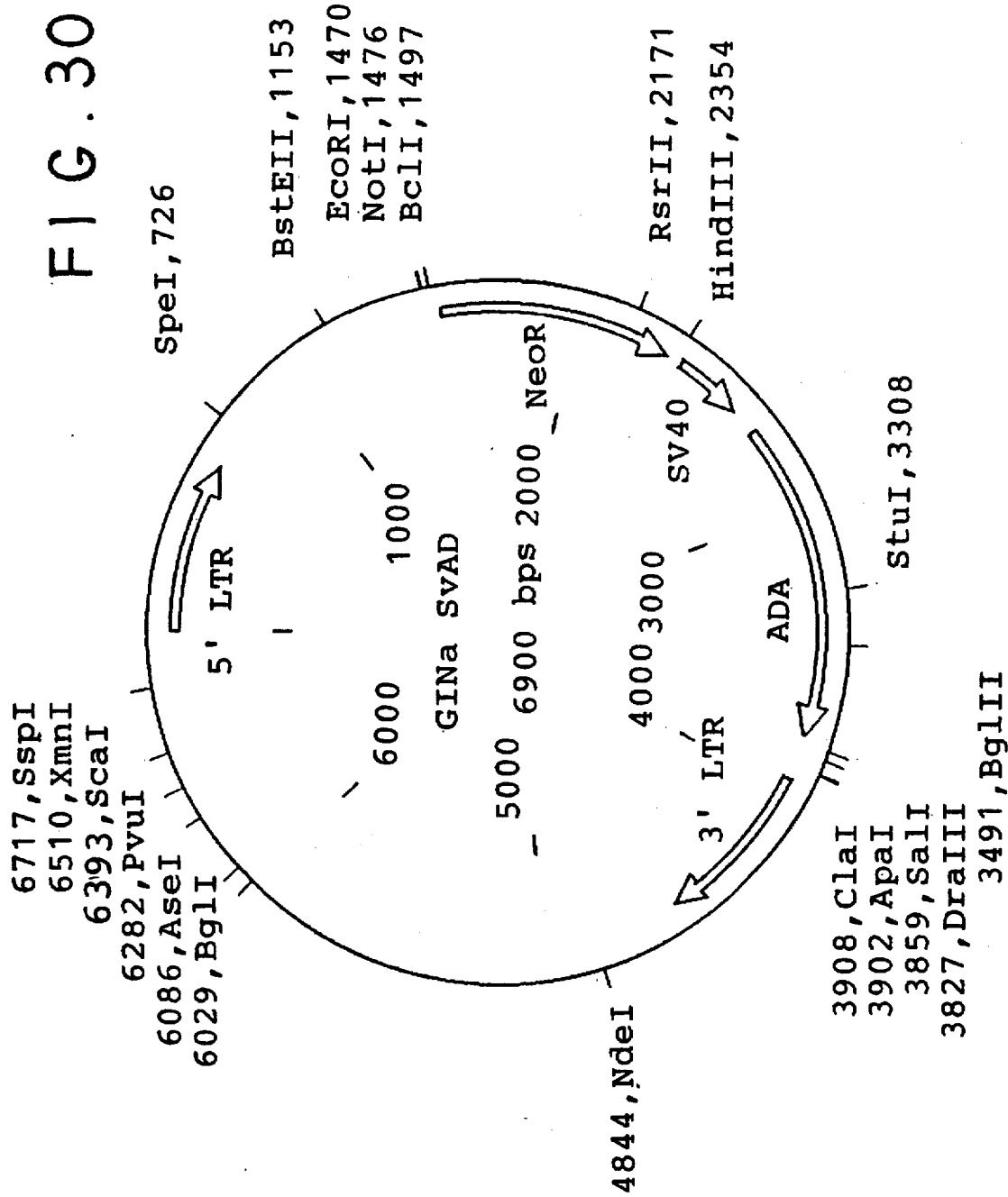
FIG. 30. Map of plasmid pG1NaSvAd.

EXAMPLE 13 pG1Na is cut with HindIII and SalI, and the ends are filled in with Klenow. pB2SA (FIG. 29), which is a pB2 plasmid which is modified to contain an SV40 promoter controlling an ADA gene, is cut with EcoRI, and the ends are filled in with Klenow. An end-filled EcoRI fragment from pB2SA containing an SV40 promoter and the human ADA gene is ligated to the end-filled HindIII/SalI digested pG1Na to form pG1NaSvAD. (FIG. 30).

EXAMPLE 14

An XhoI-BamHI fragment containing the chicken β-actin promoter (Quitschke, et al., J. Biol. Chem., Vol. 264, No. 16, pgs. 9539–9546 (1989)) was cloned into SalI-BamHI digested pG1Na by standard techniques to form pG1NaBcX.

pG1NaBcX was cut at SalI, and a SalI restriction fragment containing the human ADA gene was ligated into the cut pG1NaBcX to form pG1NaBcAD.

EXAMPLE 15

Fragments containing one of the Cb, Cd, Cd1, Cd2, or Cd3 genes, each of which encode soluble CD4, were cloned into various "backbone" vectors hereinabove described to form retroviral vectors containing CD4 genes. Cd1 encodes the immunoglobulin-like V1 and V2 domains of CD4 in the order of V1V2V1V1. Cd2 encodes a tandem repeat of the V1 and V2 domains in the order of V1V2V1V2. Cd3 encodes three tandem copies of the V1 and V2 domains in the order of V1V2V1V2V1V2. The CD4 gene fragments, "backbone" vectors and restriction sites at which such vectors were cut, and the resulting CD4 vectors are given in Table VI below.

TABLE VI

| Gene Fragment | Backbone vector | CD4 Vector |
| --- | --- | --- |
| BglII-Cb-XhoI | pG1N2SvBg (cut at BglII and XhoI) | pG1N2SvCb |
| BglII-Cd-HindIII | pG1NaSvBg (cut at BglII and HindIII) | pG1NaSvCd |
| BglII-Cd-HindIII | pG1NaCvBg (cut at BglII and HindIII) | pG1NaCvCd |
| SmaI-Cd1-NruI | pG1NaSvBg (cut at BglII and HindIII-fill in ends with Klenow) | pG1NaSvCd1 |
| Sma-Cd1-NruI | pG1NaCvBg (cut at BglIII-fill in ends with Klenow) | pG1NaCvCD1 |
| SmaI-Cd1-NruI | pG1XSvNa (cut at SnaBI) | pG1Cd1SvNa |
| NruI-Cd2-HindIII | pG1NaSvBg (cut at BglII and HindIII-fill in ends with Klenow) | pG1NaSvCd2 |
| NruI-Cd2-HindIII | pG1NaCvBg (cut at BglII and HindIII-fill in ends with Klenow) | pG1NaCvCd2 |
| NruI-Cd3-HindIII | pG1NaCvBg (cut at BglII and HindIII-fill in ends with Klenow) | pG1NaCvCd3 |

Figure 31:
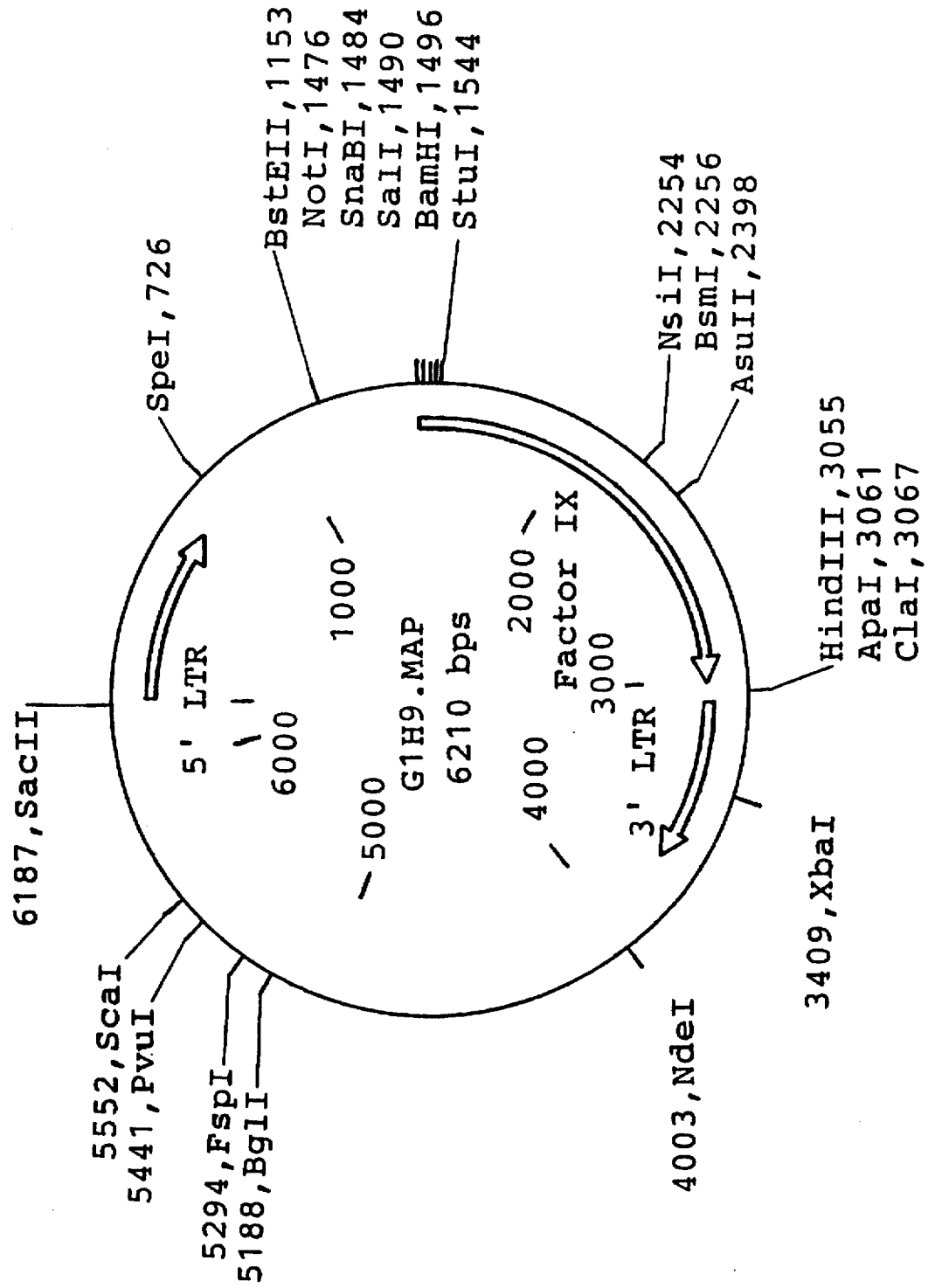
FIG. 31. Map of plasmid pG1H9.

EXAMPLE 16 pG1 is cut with BamHI and HindIII. pLIXSNL (Palmer, et al., Blood, Vol. 73, No. 2, pgs. 438–445 (February 1989)), which contains a Factor IX gene, an SV40 promoter, and a neo$^R$gene, is also cut with BamHI and HindIII. The resulting BamHI-HindIII fragment, which contains the Factor IX gene, is then ligated to the BamHI-HindIII digested pG1 to form pG1H9. (FIG. 31).

Figure 32:
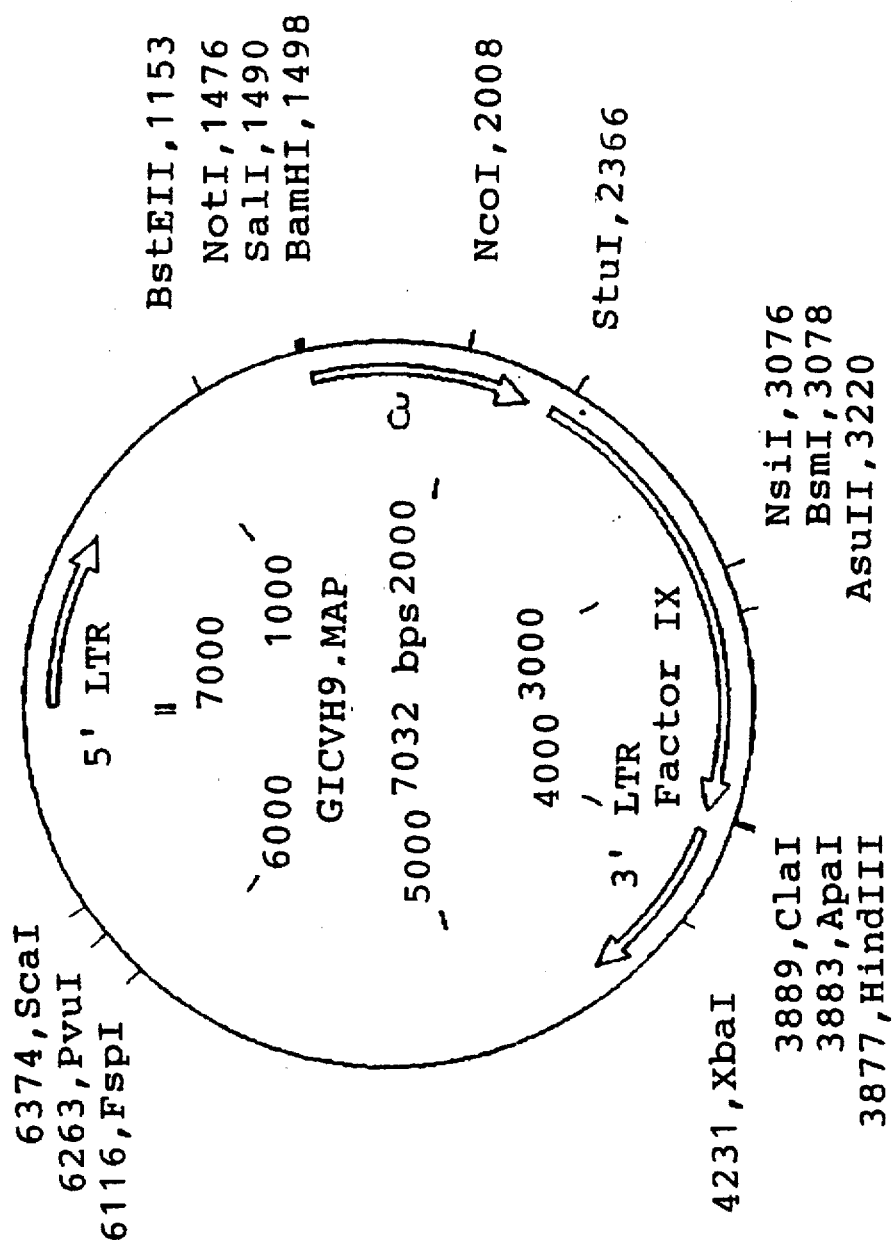
FIG. 32. Map of plasmid pG1CvH9.

EXAMPLE 17 pG1H9 is cut with SalI and BamHI. pCvBg is cut with SalI and BglII, and a SalI-BglII fragment containing the CMV promoter is ligated to the SalI-BamHI digested pG1H9 to form pG1CvH9. (FIG. 32.)

Figure 33:
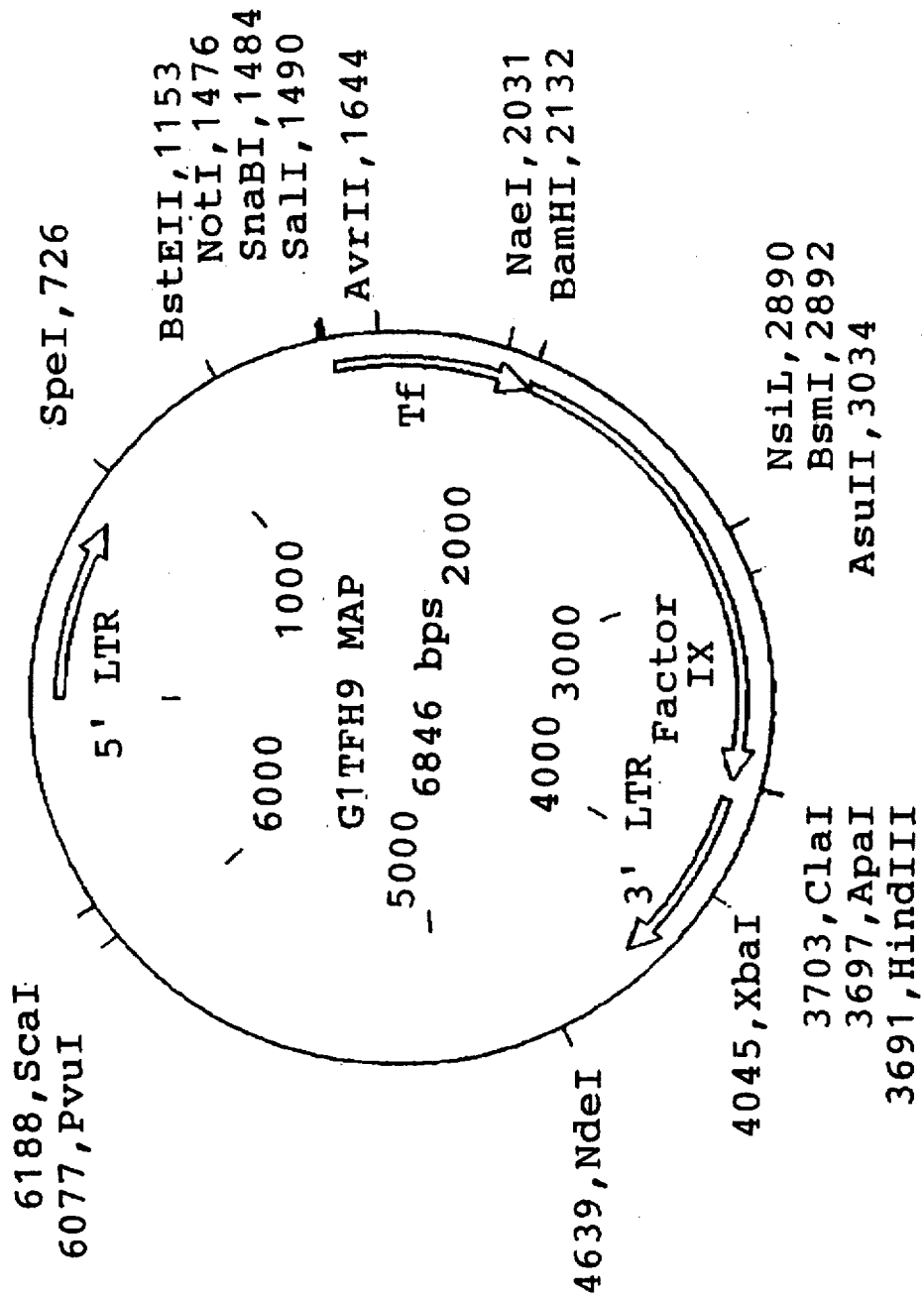
FIG. 33. Map of plasmid pG1TfH9.

EXAMPLE 18 pG1H9 is cut with SalI and BamHI. A fusion gene of the mouse transferrin promoter (MTf) and the human growth hormone (hGH) gene, also known as MTfhGH (Idzerda, et al., Mol. and Cell. Biol., Vol. 9, No. 11, pgs. 5154–5162 (Nov. 1989)), is cut with HindIII, blunted, and SalI linkers are added. A SalI-BamHI fragment is then isolated which contains the MTf promoter. This fragment is then ligated to SalI-BamHI digested pG1H9 to form pG1TfH9. (FIG. 33.)

Figure 34:
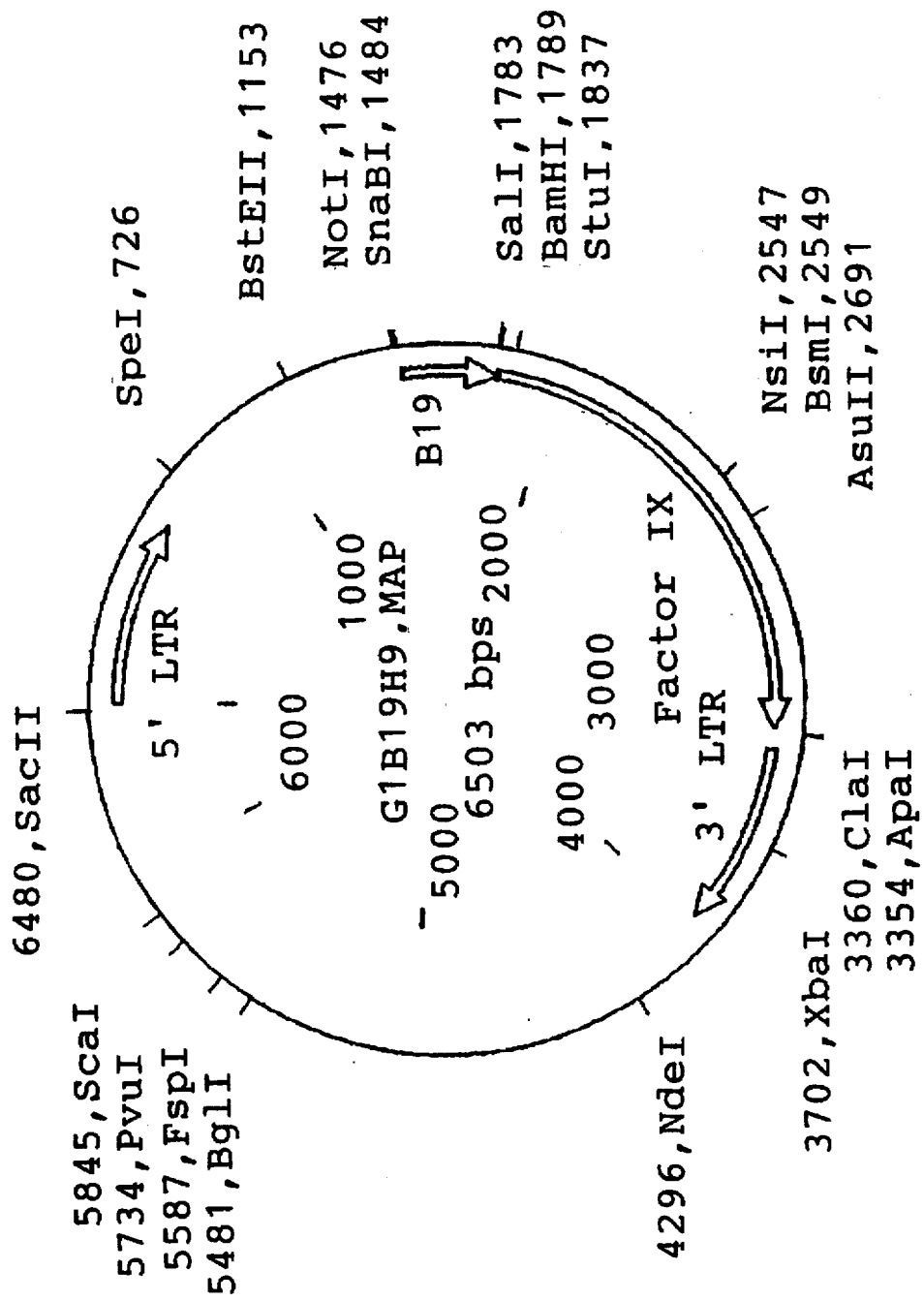
FIG. 34. Map of plasmid pG1B19H9.

EXAMPLE 19 pG1H9 is cut with SalI and BamHI. An XhoI-BamHI fragment which includes the B19 parvovirus promoter is then cut from pUC8X (Liu, et al., Virology, Vol. 182, pgs. 361–364 (1991)). This fragment is then ligated to the SalI-BamHI digested pG1H9 to form pG1B19H9. (FIG. 34).

Figure 35:
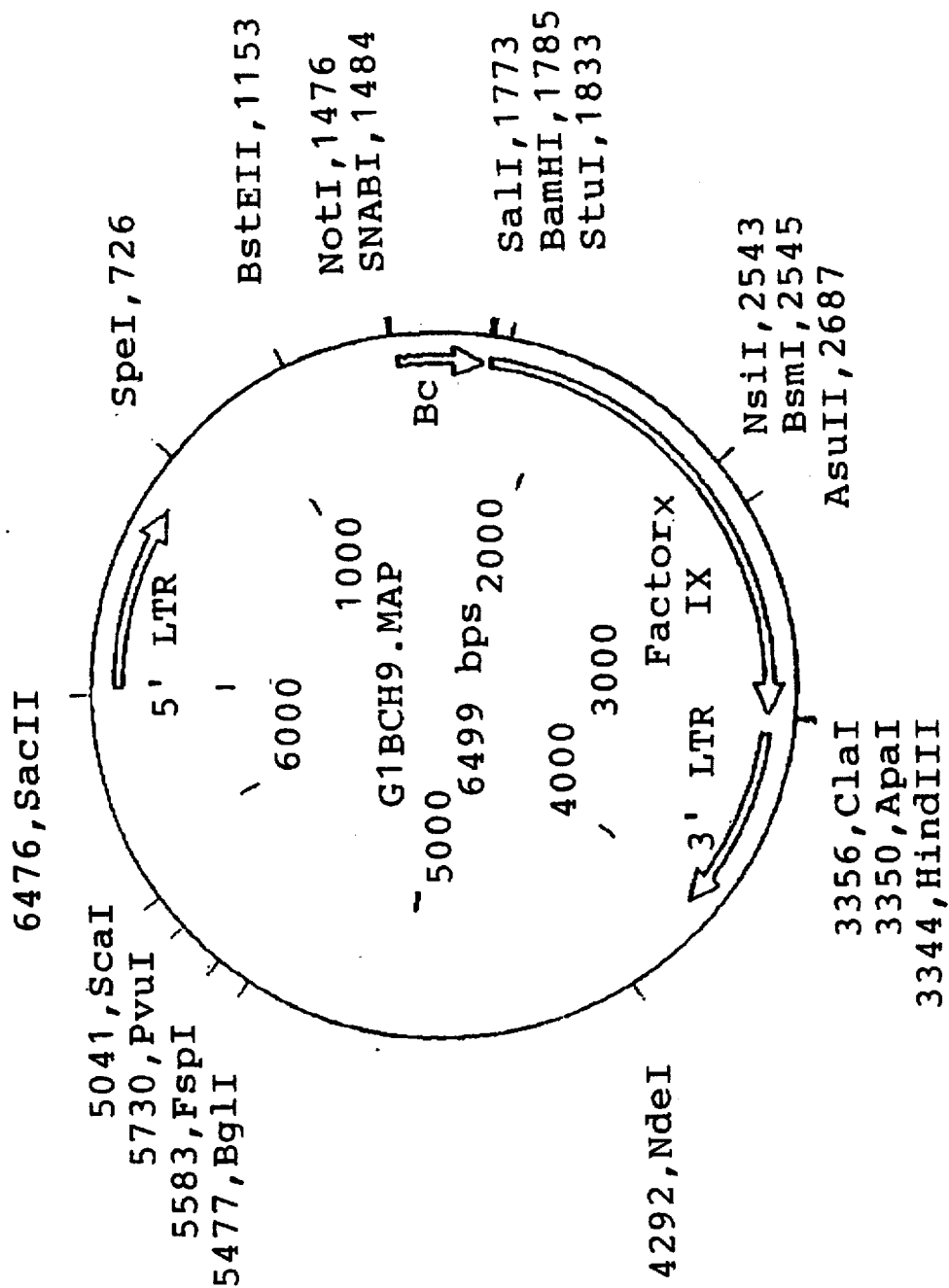
FIG. 35. Map of plasmid pG1BcH9.

EXAMPLE 20 pG1H9 is cut with SalI and BamHI. an XhoI-BamHI fragment which includes the chicken β-actin promoter (Quitschke, et al., 1989) is isolated from a pUC vector. This fragment is then ligated into the SalI-BamHI digested pG1H9 to form pG1BcH9. (FIG. 35.)

EXAMPLE 21

This example describes the production of vector producer cell lines from pG1NaSvCd, pG1NaCvCd, and pG1NaCvCd3. The producer cell lines were prepared by transfection into the PE501 cell line followed by transinfection into the PA317 cell line, and the titers of clones were determined according to Example 1. Producer clones generated from pG1NaSvCd generated from $1\times10^4$ to $1.1\times10^5$ G418 resistant colony-forming units per ml. The producer cells secreted from 500 to 2,600 ng/$10^6$ cells/24 hrs. of the V1V2 domains of CD4 based on Western blot and ELISA analysis. Producer clones generated from pG1NaCvCd were identified which generated from $1\times10^3$ to $9\times10^4$ G418 resistant colony-forming units per ml. The producer cells secreted from 400 to 1,300 ng/$10^6$ cells/24 hrs. of the V1V2 domains of CD4 based on Western blot and ELISA analysis. Producer clones generated from pG1NaCvCd3 were identified which generated $3.5\times10^2$ G418 resistant colony-forming units from PE501, and which generated $9.5\times10^4$ G418 resistant colony-forming units when transfected into PA317 cells. Producer cells secreted 150 ng/$10^6$ cells/24 hrs. based on ELISA assay.

It is to be understood, however, that the scope of the present invention is not to be limited to the specific embodiments described above. The invention may be practiced other than as particularly described and still be within the scope of the accompanying claims.

What is claimed is:

1. A retroviral vector, said vector including a 3' LTR; a 5' LTR; and a multiple cloning site having a length no greater than about 70 base pairs, wherein said multiple cloning site is located between the 5' LTR and 3' LTR of said retroviral vector, and the 5' end of said multiple cloning site is no greater than about 895 base pairs from the 3' end of the 5' LTR, and the 3' end of the multiple cloning site is no greater than about 40 base pairs from the 5' end of the 3' LTR, and said multiple cloning site includes the NotI, SnaBI, SalI, BamHI, XhoI, HindIII, ApaI, and ClaI cloning sites.

2. The retroviral vector of claim 1 wherein said retroviral vector is pG1 as shown in FIG. 1.

3. The retroviral vector of claim 1 wherein the 3' LTR is mutated by changing bases in the promoter sequence while maintaining the length of the non-mutated 3' LTR, such that said promoter sequence becomes non-functional.

4. A retroviral vector, said vector including a heterologous gene, said retroviral vector including the heterologous gene having been prepared from the vector of claim 1 by inserting said heterologous gene into said multiple cloning site.

5. The retroviral vector of claim 1 wherein said 3'LTR is obtained from Moloney Murine Leukemia Virus.

6. The retroviral vector of claim 1 wherein said 5'LTR is obtained from Moloney Sarcoma Virus.

7. A cloning system for the manipulation of genes in retroviral vectors, comprising:

a retroviral vector including a 3' LTR, a 5' LTR, and a multiple cloning site having a length no greater than about 70 base pairs, wherein said multiple cloning site is located between the 5' LTR and 3' LTR of said retroviral vector, and the 5' end of said multiple cloning site is located between the 5' LTR and 3' LTR of said retroviral vector, and the 5' end of said multiple cloning site is no greater than about 895 base pairs from the 3' end of the 5' LTR, and the 3' end of said multiple cloning site is no greater than about 40 base pairs from the 5' end of the 3' LTR, and said multiple cloning site including the NotI, SnaBI, SalI, BamHI, XhoI, HindIII, ApaI, and ClaI cloning sites; and a shuttle cloning vector including the SphI, NotI, SnaBI, SalI, SacII, AccI, NruI, BglII, NcoI, XhoI, HindIII, ApaI, and SmaI cloning sites, and said shuttle cloning vector including at least one desired gene sequence capable of being transferred from said shuttle cloning vector to said retroviral vector.

8. A retroviral vector produced by transferring said at least one desired gene from said shuttle vector of claim 6 to said retroviral vector of claim 7.

9. The system of claim 7 wherein said 3'LTR of said retroviral vector is obtained from Moloney Murine Leukemia Virus.

10. The system of claim 7 wherein said 5'LTR is obtained from Moloney Sarcoma Virus.

11. The cloning system of claim 7 wherein said shuttle cloning vector includes a multiple cloning site having the sequence shown in FIG. 4.

12. A retroviral vector including a 3' LTR, wherein the 3' LTR is mutated, by changing bases in the promoter sequence(s) while maintaining the length of the non-mutated 3' LTR such that said promoter sequence becomes non-functional.

13. The retroviral vector of claim 12 wherein said vector further includes a mutation(s) of the enhancer sequence(s), by changing bases in the enhancer sequence(s) while maintaining the length of the non-mutated 3' LTR, such that said enhancer sequence(s) becomes non-functional.

14. The retroviral vector of claim 12 wherein the integrator sequence is maintained.

15. The retroviral vector of claim 12 wherein the 3' LTR of said retroviral vector includes the sequence shown in FIG. 8.

16. A packaging cell transfected with the retroviral vector of claim 4.

17. Infectious viral particles generated from the retroviral vector of claim 4.

18. The retroviral vector of claim 4 wherein said vector is pG1Na as shown in FIG. 10.

19. The retroviral vector of claim 4 wherein said vector is pG1Ns as shown in FIG. 11.

20. The retroviral vector of claim 4 wherein said vector is pG1NaSvBg as shown in FIG. 14.

21. The retroviral vector of claim 4 wherein said vector is pG1XSvNa as shown in FIG. 19.

Figure 23:
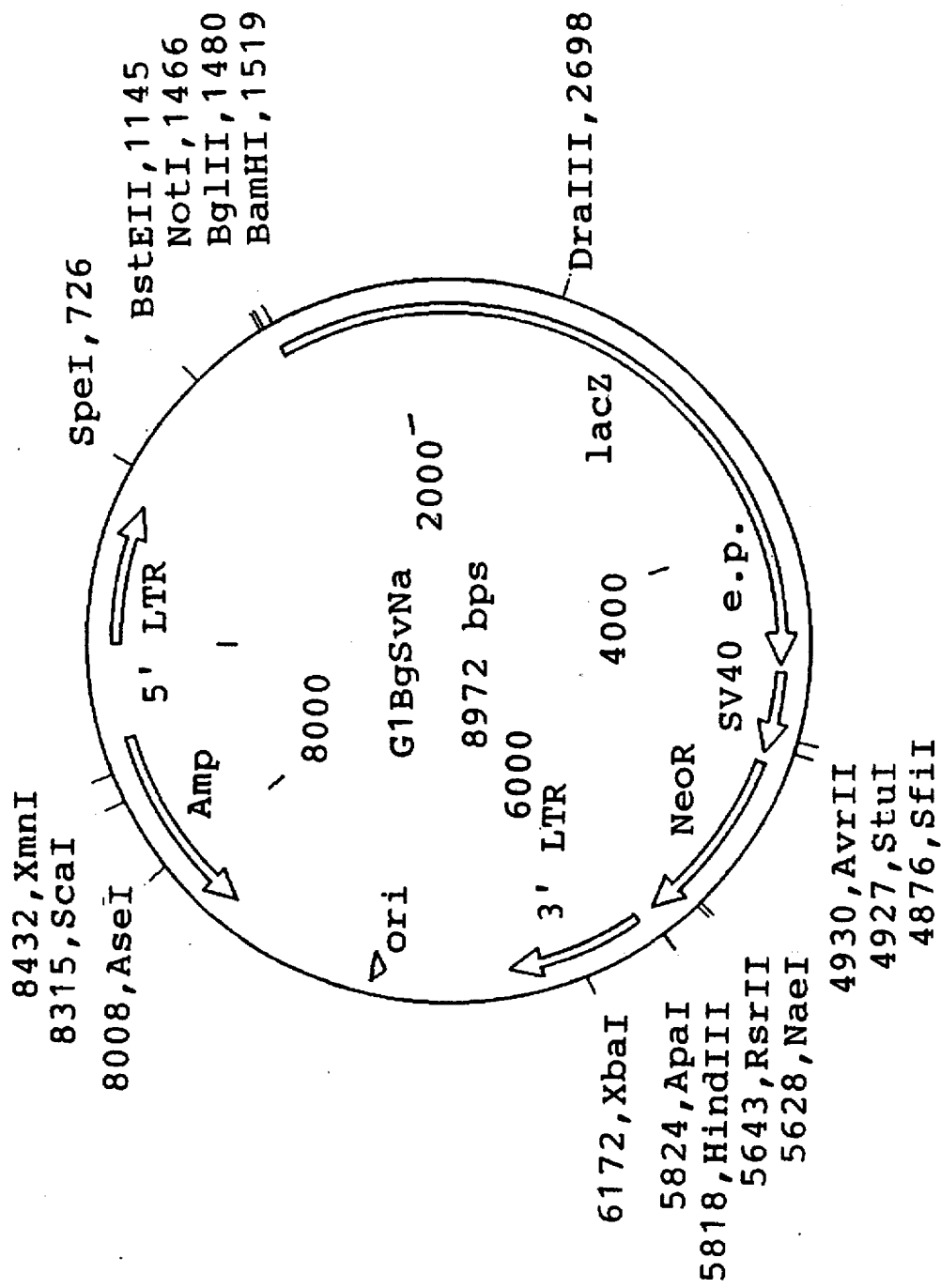
FIG. 23. Map of plasmid pG1BgSvNa.

22. The retroviral vector of claim 4 wherein said vector is pG1BgSvNa as shown in FIG. 23.

23. The retroviral vector of claim 4 wherein said vector is pG1H9 as shown in FIG. 31.

24. The retroviral vector of claim 4 wherein said heterologous gene is selected from the group consisting of the neomycin resistance gene; the β-galactosidase gene; the adenosine deaminase gene; the CD4 gene; the Factor IX gene; the TNF-α gene; the Interferon-α gene, the Interleukin-1β gene; the Interleukin-2 gene; the Interleukin-2 receptor gene; the Interleukin-4 gene; and the GM-CSF gene.

25. A eukaryotic cell transfected with the infectious viral particles of claim 17.

26. A retroviral vector, said vector including a 3' LTR; a 5' LTR; and a multiple cloning site having a length no greater than about 70 base pairs, wherein said multiple cloning site is located between the 5' LTR and 3' LTR of said retroviral vector, and the 5' end of said multiple cloning site is no greater than about 895 base pairs from the 3' end of the 5' LTR, and the 3' end of the multiple cloning site is no greater than about 40 base pairs from the 5' end of the 3' LTR, and said multiple cloning site includes at least four restriction enzyme sites and at least two of the restriction enzyme sites of said multiple cloning site being selected from the group consisting of NotI, SnaBI, SalI, and XhoI, cloning sites.

27. A retroviral vector, said vector including a heterologous gene, said vector including a heterologous gene having been prepared from the vector of claim 26 by inserting said heterologous gene into said multiple cloning site.

* * * * *